(12) United States Patent
Peschl

(10) Patent No.: US 12,350,393 B2
(45) Date of Patent: Jul. 8, 2025

(54) SURFACE RADIATOR, DEVICE COMPRISING THE SURFACE RADIATOR AND USE OF THE SURFACE RADIATOR

(71) Applicant: Peschl Ultraviolet GmbH, Mainz (DE)

(72) Inventor: Alexander Peschl, Mainz (DE)

(73) Assignee: Peschl Ultraviolet GmbH, Mainz (DE)

( * ) Notice: Subject to any disclaimer, the term of this patent is extended or adjusted under 35 U.S.C. 154(b) by 0 days.

(21) Appl. No.: 18/849,521

(22) PCT Filed: Apr. 7, 2022

(86) PCT No.: PCT/EP2022/059279
§ 371 (c)(1),
(2) Date: Sep. 22, 2024

(87) PCT Pub. No.: WO2023/193915
PCT Pub. Date: Oct. 12, 2023

(65) Prior Publication Data
US 2025/0161508 A1    May 22, 2025

(51) Int. Cl.
*F21V 31/00* (2006.01)
*A61L 2/10* (2006.01)
(Continued)

(52) U.S. Cl.
CPC ................. *A61L 2/10* (2013.01); *A61L 2/26* (2013.01); *B01J 19/0013* (2013.01);
(Continued)

(58) Field of Classification Search
CPC .......... A61L 2/10; A61L 2/26; A61L 2202/11; A61L 2202/121; A61L 2202/123;
(Continued)

(56) References Cited

U.S. PATENT DOCUMENTS

2017/0030567 A1    2/2017    Sun et al.
2017/0167712 A1    6/2017    Melzner
(Continued)

FOREIGN PATENT DOCUMENTS

CN    108180403 A    6/2018
DE    202011050253 U1    8/2011
(Continued)

*Primary Examiner* — Xiuyu Tai
(74) *Attorney, Agent, or Firm* — Smartpat PLC

(57) ABSTRACT

A surface radiator includes a light-emitting semiconductor component and a housing body. The housing body has a cooling channel forming part of a fluid path from an inlet opening to a return opening. A transparent emission window overlies the light-emitting semiconductor component. The housing body provides an attachment surface spaced apart from the emission window for the light-emitting semiconductor component. The arrangement of the emission window on the housing body is formed in a fluid-tight manner. The housing body, the semiconductor component and the emission window delimit an emission chamber. The fluid path is defined by a first cooling channel, which extends from the inlet opening through the housing body to an orifice opening, the emission chamber, and a second cooling channel, which extends from the discharge opening through the housing body to the return opening. The coolant is an electrically insulating liquid, which is transparent for the incident radiation.

14 Claims, 11 Drawing Sheets

(51) Int. Cl.
*A61L 2/26* (2006.01)
*B01J 19/00* (2006.01)
*B01J 19/12* (2006.01)
*H10H 29/24* (2025.01)
*H10H 29/85* (2025.01)

(52) U.S. Cl.
CPC ............ *B01J 19/123* (2013.01); *H10H 29/24* (2025.01); *H10H 29/8586* (2025.01); *A61L 2202/11* (2013.01); *A61L 2202/121* (2013.01); *A61L 2202/123* (2013.01); *B01J 2219/0871* (2013.01); *B01J 2219/0879* (2013.01); *B01J 2219/1203* (2013.01)

(58) Field of Classification Search
CPC ....... A61L 2209/12; A61L 9/20; H10H 29/24; H10H 29/8586; B01J 19/0013; B01J 19/123; B01J 2219/0871; B01J 2219/0879; B01J 2219/1203; B01J 19/122; C02F 1/325; C02F 2201/3228; C02F 2201/3222; C02F 2201/328; C02F 2303/04; C02F 2201/3227; F21V 23/006; F21V 29/503; F21V 29/508; F21V 29/59; F21V 31/005; F21V 2105/10; F21V 2115/10

See application file for complete search history.

(56) References Cited

U.S. PATENT DOCUMENTS

| | | |
|---|---|---|
| 2020/0124266 A1 | 4/2020 | Di et al. |
| 2021/0039063 A1* | 2/2021 | Amador ................. B01J 19/127 |
| 2022/0072871 A1 | 3/2022 | Meyer et al. |
| 2022/0204898 A1 | 6/2022 | Peschl et al. |

FOREIGN PATENT DOCUMENTS

| | | |
|---|---|---|
| DE | 202014103329 U1 | 9/2014 |
| DE | 102014012218 A1 | 2/2016 |
| DE | 102014012219 A1 | 2/2016 |
| DE | 102016224064 A1 | 6/2018 |
| EP | 2701473 A2 | 2/2014 |
| KR | 20160100712 A | 8/2016 |
| WO | 2016026576 A1 | 2/2016 |
| WO | 2020148289 A1 | 7/2020 |
| WO | 2020228980 A1 | 11/2020 |

\* cited by examiner

A-A

C-C

Fig. 5
Fig. 6
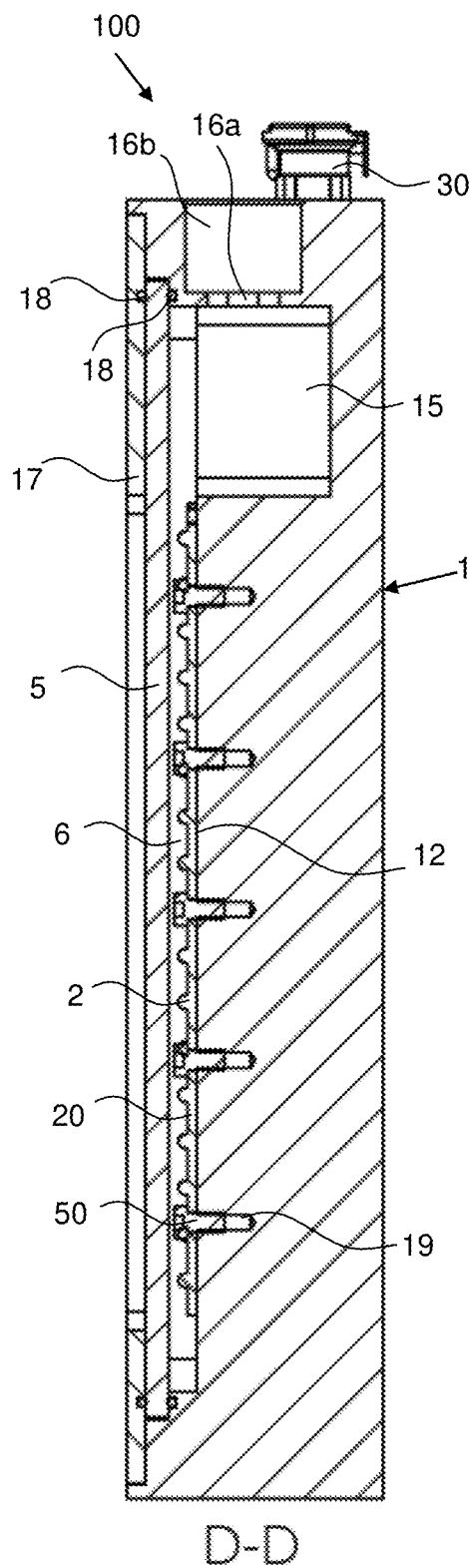
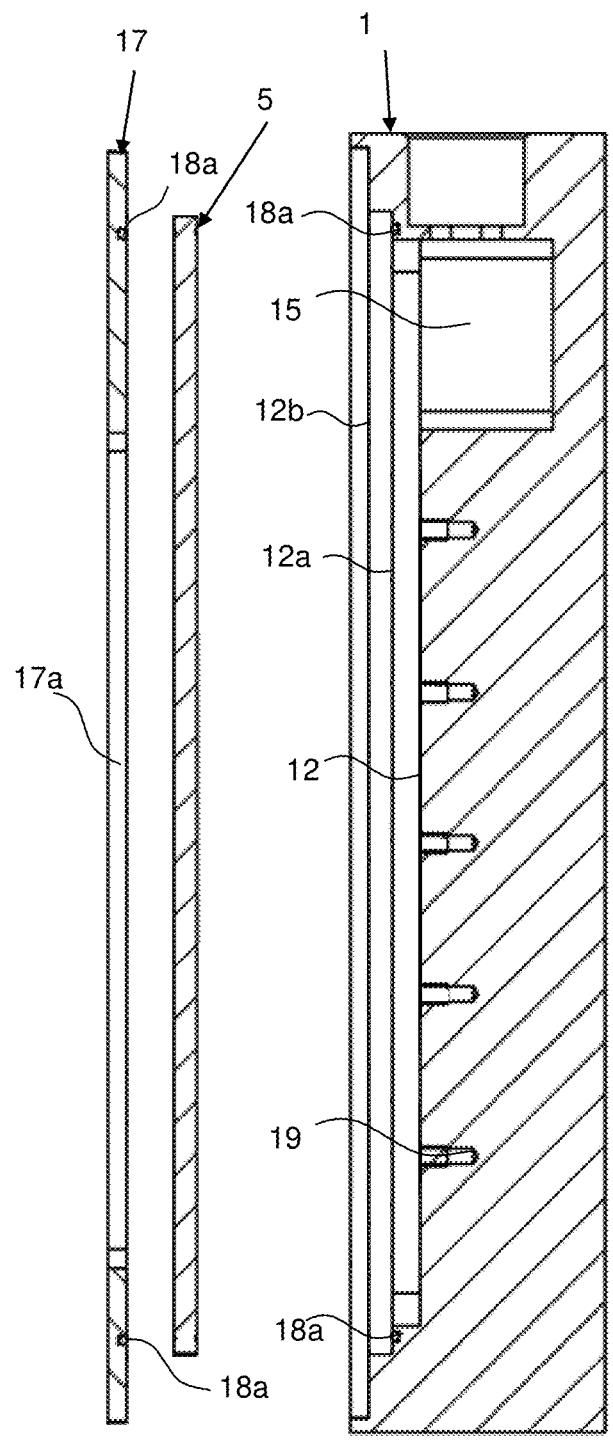

Fig. 7
Fig. 8
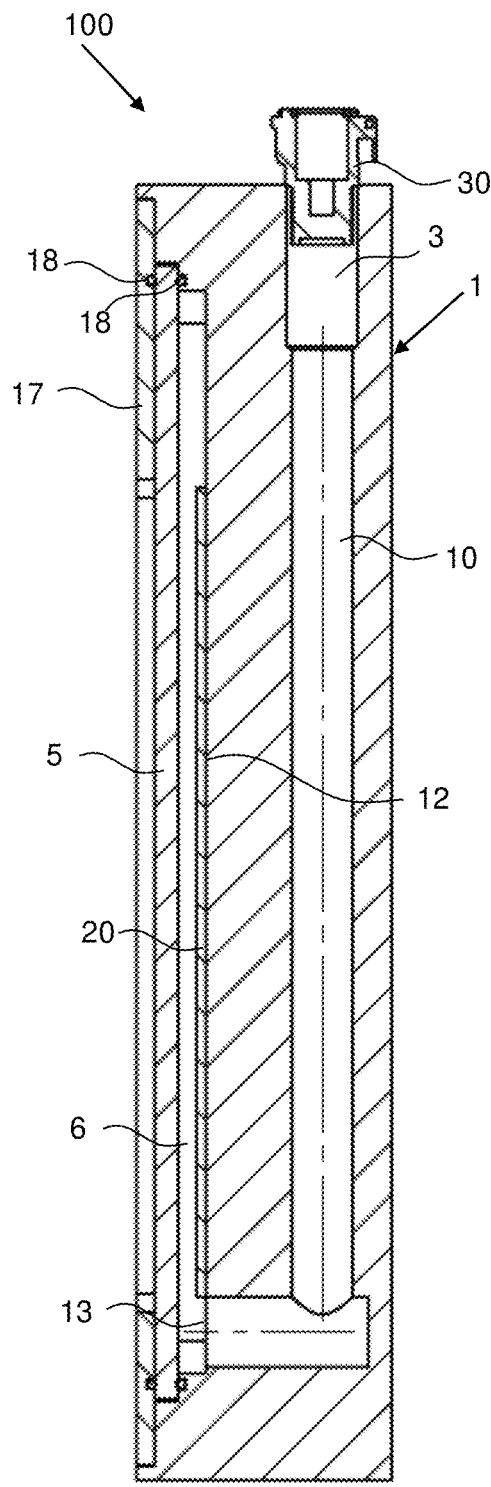
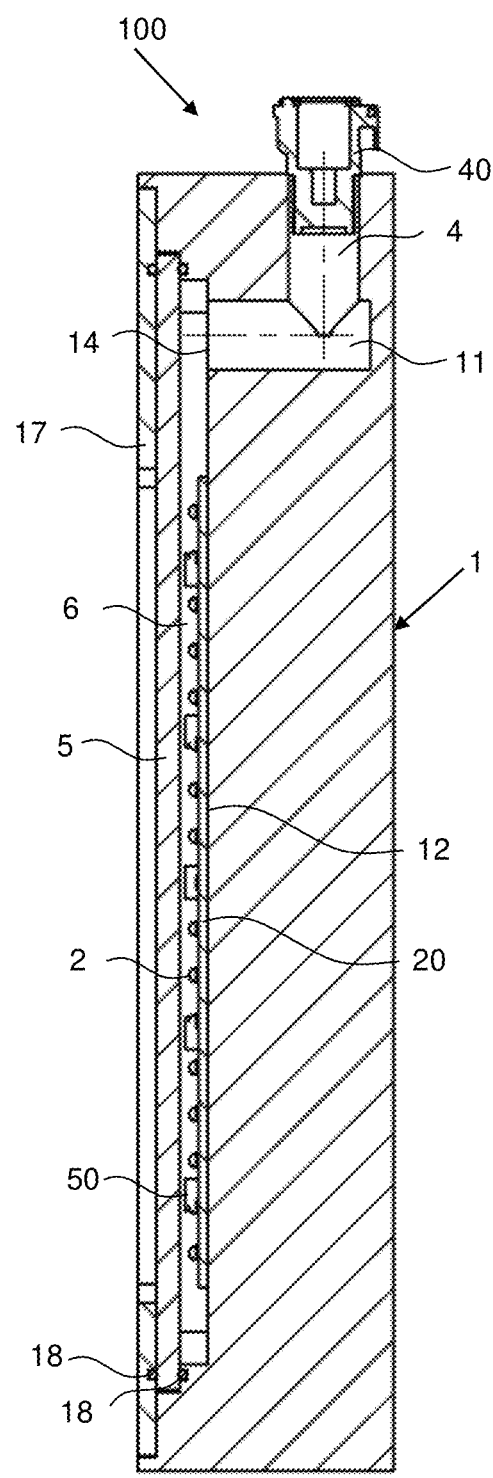
E-E
F-F

SURFACE RADIATOR, DEVICE COMPRISING THE SURFACE RADIATOR AND USE OF THE SURFACE RADIATOR

CROSS-REFERENCE TO RELATED APPLICATION

This application is a national stage application, filed under 35 U.S.C. § 371, of International Patent Application PCT/EP2022/059279, filed on Apr. 7, 2022.

TECHNICAL FIELD

The disclosure relates to a surface radiator comprising a light-emitting semiconductor component as well as a device equipped with such a surface radiator for lighting, for carrying out a photochemical reaction or for disinfection, and a use of such a surface radiator also for carrying out a photochemical reaction or for disinfection.

BACKGROUND

It is known from the prior art to use surface radiators with directed light emission in order to attain an even lighting of a surface. A surface radiator thus has a unilateral emission characteristic, wherein the emission angle can vary. Due to the significantly smaller energy consumption, surface radiators with light-emitting semiconductor components, such as light-emitting diodes (LED) are increasingly also used for the large-surface emission of light. LEDs have a long service life and high switching resistance even in the case of spontaneously full luminous flux. Even though LEDs are not heat radiators, high temperatures, which do in fact occur during operation as a function of the arrangement and the performance of the LEDs, significantly shorten the service life of the LEDs, however. In order to avoid this disadvantageous influence, LEDs are often not operated at nominal power but below it—associated with lower lighting performance. In order to nonetheless attain a desired light quantity, the number of the used LEDs is then increased.

To form surface radiators, the LEDs are arranged downstream from an emission window on an essentially flat, mostly rectangular carrier surface by means of a housing frame and can be surrounded by a reflector frame in order to set the emission characteristic. In the case of surface radiators with a very large number of LEDs, the latter can be fastened in groups on a respective printed circuit board, on which conductor tracks for electrically contacting the LEDs and optionally also ballasts (LED drivers) for controlling purposes are provided. The conductor tracks usually run towards an edge of the printed circuit board in order to provide for the electrical connection there. Disadvantageously, the heat developing during operation can only be discharged insufficiently from the printed circuit board.

EP 2 701 473 A2 thus proposes to use a printed circuit board, which provides conductor track segments formed to be flat, which form a comparatively large boundary surface with a surrounding area of the printed circuit board, for an LED surface radiator. The waste heat generated by the LEDs is to be dissipated from the printed circuit board into the surrounding area by means of the conductor track segments, which are formed to be flat.

To significantly improve the heat dissipation, metal housings, mostly of aluminum, are used. A lighting device with a plurality of LED, which is arranged on a carrier unit formed as printed circuit board, is thus known, e.g., from DE 20 2011 050 253 U1. The lighting device further has an H-shaped aluminum profile body comprising two sections, wherein the carrier unit comprising the LEDs is arranged on a first section of the profile body. A light-permeable polymer sleeve encloses the carrier unit comprising the LEDs and the first section. The second section of the profile body, which protrudes from the polymer cladding, serves the purpose of heat dissipation to a housing body.

In the industrial use with high-performance diodes, which are operated for photochemical reactions with a high light yield or radiation intensity with high currents, respectively, an even more effective heat dissipation is required in order to maintain the service life of the LEDs.

The WO2020/148289 A1 describes a flat light source with LEDs for curing printing inks or varnishes, wherein at least one light-emitting semiconductor component (as LED module comprising a corresponding printed circuit board) is arranged on a carrier plate. The light source further has a distributor element formed as housing, on which an emission window is arranged, which overlies the at least one LED module. The housing-distributor element further has a cooling channel, which is connected to connections for the inlet and return of a cooling fluid via a connecting element. Several carrier plates comprising LED modules can be arranged on the housing-distributor element, wherein a surface of each carrier plate facing away from the LED module is formed as cooling surface, which is arranged on the distributor element in a sealed manner. The cooling surface thus partly delimits a fluid path, which is connected to the cooling channel in the distributor element via channel branches.

DE 20 2014 103329 U1 relates to a headlight with an LED light source, which is likewise liquid-cooled. To improve the cooling, the LED light source can be arranged on a cooler with separate liquid cooling or can be fastened to a cooling element, which is arranged with the LED light source within the housing and around which the coolant likewise flows.

US 2017/030567 A1 likewise discloses a liquid-cooled LED light, and a liquid-cooled laser light-emitting device is known from CN 108 180 403 A.

KR 2016 0100712 A discloses an LED surface radiator comprising a housing body, in which two cooling channels are formed, which are covered by means of a metal plate comprising LEDs fastened thereon. Fluid openings, which each communicate with one of the two cooling channels, are formed in the metal plate on both sides adjacent to the LEDs. An emission window spaced apart from the printed circuit board comprising the LEDs is connected in a fluid-tight manner to the housing body, so that a fluid path for an electrically insulating and transparent coolant extends between the cooling channels through the fluid openings along the LEDs.

SUMMARY

It is an object of the present disclosure to provide a surface radiator, which is improved with respect to the heat dissipation and the thermal decoupling of the light-emitting semiconductor components.

This object is solved by means of a surface radiator as disclosed and claimed.

The further object of providing a device, which is improved with respect to the heat dissipation and the thermal decoupling of the light-emitting semiconductor components of a surface radiator, for lighting, carrying out a photochemical reaction or disinfection, is solved by means of a device as disclosed herein.

A use of a surface radiator, which is improved with respect to the heat dissipation and the thermal decoupling of the light-emitting semiconductor components, is disclosed by means of the use of the device as disclosed herein.

According to a first embodiment, a surface radiator has at least one light-emitting semiconductor component and a housing body comprising at least one cooling channel for a coolant. A surface radiator thereby usually comprises a plurality of light-emitting semiconductor components (LEDs), which are arranged next to one another at regular intervals on an essentially flat surface for a unilaterally directed light emission. The cooling channel forms at least a part of a fluid path, which extends from an inlet opening for the coolant to a return opening for the coolant. The inlet opening and the return opening are formed on the housing body and are preferably provided for connection to a coolant circuit. An emission window, which defines a front side of the surface radiator, on which the unilateral directed light emission takes place, is arranged on the housing body. A plate or disk of a material, which is transparent for an incident radiation emitted by the at least one light-emitting semiconductor component and which—depending on the planned use of the surface radiator for lighting, for carrying out a photochemical reaction or for disinfection—is defined by at least one predetermined wavelength or at least one predetermined wavelength range of electromagnetic radiation, is hereby understood as "emission window". "Transparent" means hereby that the emission window for incident radiation has a transmission degree of at least 75%. The dimensioning of the emission window and the arrangement thereof on the hosing body corresponds to the arrangement of the one LED or the several LEDs, so that the emission window overlies the at least one light-emitting semiconductor component in a flat manner.

The housing body itself, without an additional carrier structure as required in the prior art, thereby provides a fastening surface, which is spaced apart from the emission window, for the at least one light-emitting semiconductor component, wherein the fastening surface for arrangement of the LED(s) corresponds to the emission window. The arrangement of the emission window on the housing body is thereby formed in a fluid-tight manner, so that a sealed emission chamber is delimited by the housing body, the semiconductor component and the emission window. The fluid path provided for cooling the LED is then defined by i) at least one first cooling channel, which extends from the inlet opening through the housing body to one or optionally several orifice opening(s), which is formed on a first side next to the fastening surface and leads into the emission chamber, and ii) the emission chamber from the orifice opening all the way to one or several discharge opening(s), which is or are formed, respectively, on a second side facing away from the first side next to the fastening surface in the housing body, so that the fastening surface lies between the orifice opening and the discharge opening and the emission chamber is filled completely with the coolant and iii) at least one second cooling channel, which extends from the discharge opening through the housing body to the return opening.

Due to the fact that the coolant thus floods the emission chamber and comes into direct contact with the LEDs, in order to more effectively dissipate the heat generated by the LEDs during operation, the coolant is an electrically insulating liquid, which is transparent for the incident radiation emitted by the light-emitting semiconductor component and ensures an improved heat transfer than with a gaseous cooling medium or air due to the specific thermal capacity, density and the coefficient of thermal conductivity. Transparency is understood herein as a transmission degree of at least 75% for the incident radiation with respect to the path length, which is defined by the distance between LED and emission window. Advantageously, not only heat can be absorbed by the LEDs by means of the flooding of the emission chamber with the liquid coolant, which is supplied from the first cooling channel through the orifice opening and which is dissipated through the discharge opening into the second cooling channel, but heat, which can be output to the outside of the surface radiator, can optionally also be absorbed from the surrounding area via the emission window, so that a heat accumulation between LEDs and emission window is avoided, the temperature of the LED is kept constant and a thermal decoupling of the surface radiator from the surrounding area is attained. A further advantage of the flooding of the emission chamber with the liquid coolant lies in the avoidance of condensate formation in the event of a large temperature gradient to the surrounding area or the irradiated surface, respectively.

A connecting chamber, which is open to the emission chamber, is formed on the front side in the housing body adjacent to the fastening surface. A connecting opening, which is connected to the connecting chamber, is thereby formed on the housing body, wherein at least one connecting line for connecting the at least one light-emitting semiconductor component extends at least into the connecting chamber. A ballast is either provided on a printed circuit board, by means of which a plurality of the light-emitting semiconductor components is fastened to the fastening surface. A pair of connecting contacts for a row of light-emitting semiconductor components is in each case formed on a side of the printed circuit board close to the connecting chamber, wherein each connecting contact is connected to a respective connecting line, wherein the ballast is provided between the connecting contacts and the light-emitting semiconductor components (LEDs). Or the ballast for the at least one light-emitting semiconductor component is arranged in the connecting chamber, connected to the at least one connecting line.

This means that a connecting chamber, which is open to the emission chamber, for receiving electrical connecting elements for the LED, which, like the emission chamber, is filled with the coolant, can be formed on the front side in the housing body adjacent to the fastening surface. A connecting opening is further formed on the housing body, wherein the arrangement of the connecting opening on one of the side surfaces or the rear side of the housing body like the arrangement of the inlet and return opening can be selected in an adapted manner as a function of an installation context. As electrical connecting elements for the connection to a power supply outside of the housing body, at least one connecting line for connecting the at least one light-emitting semiconductor component extends at least into the connecting chamber and optionally into or through the connecting opening.

A surface radiator further has several light-emitting semiconductor components, in particular several LEDs, which are arranged on a printed circuit board, optionally on several, by means of which the light-emitting semiconductor components are fastened to the fastening surface of the housing body. A pair of connecting contacts for a row of light-emitting semiconductor components is thereby in each case formed on a side of the printed circuit board close to the connecting chamber, wherein each connecting contact is electrically conductively connected to a respective connecting line. A "row" of LEDS hereby refers to a predetermined number of LEDs on a printed circuit board, which can preferably be arranged on a straight line over the length of a printed circuit board, but which can optionally also be arranged in a different pattern, e.g., in zigzag. A surface radiator can have a printed circuit board with a row of LEDs, preferably with several parallel rows of LEDs. By means of the arrangement of the connecting contacts on the side of the connecting chamber, the length of the connecting lines can be minimized and a line guidance through the emission chamber can be avoided, whereby not only a shading of the LEDs is prevented but line jacket materials can also be protected, e.g., against UV radiation. The electrically conductive connection of a connecting line to a connecting contact can be soldered, e.g., in order to avoid insulation resistances due to the coolant.

A ballast or LED driver, respectively, required for the operation of the LEDs can be provided on the printed circuit board between the connecting contacts and the LEDs. In order to minimize a heat input of a ballast on the LEDs, however, is preferably provided that the ballast for the light-emitting semiconductor component is arranged in the connecting chamber and is connected to the one or several connecting lines. The heat generated by the ballast is thereby not guided via the printed circuit board to the LEDs but is transferred via the coolant to the housing body, which surrounds the connecting chamber, and/or is dissipated with the coolant from the emission chamber.

A circulation of the coolant can preferably be provided, in that the coolant heated in the surface radiator is circulated, in order to output the absorbed heat again outside of the emission chamber. Further advantageously, the flooding of the emission chamber with the liquid coolant ensures an avoidance of near-field reflection between LED and emission window and prevents the presence of volatile organic hydrocarbon compounds (VOCs) in the emission chamber, which could damage the LEDs. In contrast to the use of an inert gas, such as nitrogen, it is advantageous thereby that an accelerated aging of the primary optics of the LEDs is avoided. This is so because VOCs ("volatile organic compounds"), which penetrate into the primary optics, which is usually embodied as silicone lens, cloud it and thus lower the light yield, are present in particular in chemical plants. Due to the fact that the primary optics are no longer exposed to a gaseous atmosphere but are shielded by the coolant, the aging process is slowed down significantly. In order to completely avoid the limitations in the light yield as a result of the aging process of the primary optics, it is advantageously possible in the case of a surface radiator that protective primary optics, such as silicone lenses, can be forgone in the case of the LEDs because the semiconductor chip of the LEDs is already sufficiently protected against environmental influences due to the liquid coolant.

A surface radiator is thus improved not only with respect to the cooling of the LEDs and the thermal decoupling from the surrounding area but also protects the LEDs against harmful substances. A surface radiator furthermore provides an increased total light or radiation performance, respectively, with respect to the lamps according to the prior art in an advantageous manner because the photon decoupling efficiency at the phase boundary of the diode surface to the coolant is increased in the emission chamber due to the liquid coolant and the reflection at the phase boundary between the coolant, which is present in the emission chamber, and the emission window is decreased.

In the present case, "incident radiation" is understood to be electromagnetic radiation of a certain wavelength or wavelength ranges, which are suitable for a predetermined use of the surface radiator, e.g., for lighting, carrying out a photochemical reaction or for disinfection.

A light-emitting semiconductor component can be a light-emitting diode (LED) or preferably an LED module, which consists of at least one LED and a printed circuit board, which has conductor tracks for the electrical connection of the at least one LED. A printed circuit board thereby does not correspond to a carrier structure from the prior art: LED modules, which consist of at least one LED and a printed circuit board, are likewise used there, wherein the modules are fastened to the carrier structures, such as the H-shaped carrier units or the carrier plates with cooling surfaces by means of the printed circuit board and the carrier structures are arranged on a housing body.

In the present case, LEDs are understood to be all light-emitting diodes, also organic light-emitting diodes (OLEDs), which emit electromagnetic radiation in the infrared, visible or ultraviolet wavelength ranges. LEDs can further have an emission spectrum with combined components in the infrared, visible and/or ultraviolet wavelength ranges. To adapt the radiation emitted by an LED to the intended purpose, the LEDs are usually doped differently. For the emission of UV radiation, for example, diamond, aluminum nitride, aluminum gallium nitride or aluminum gallium indium nitride are possible as doping.

According to a further embodiment of the surface radiator, the housing body can have a rear side facing away from the front side and is delimited between front side and rear side by means of side surfaces. The inlet opening and the return opening of the fluid path can be arranged jointly on one of the side surfaces or jointly on the rear side or individually on different side surfaces or individually on one of the side surfaces and the rear side in each case. The arrangement of inlet opening and return opening on rear side and/or side surfaces of the housing body can be selected in an adapted manner as a function of the installation context of the surface radiator in a higher-ranking device for lighting, in particular for carrying out a photochemical reaction or for disinfection. The housing body can further be formed for the arrangement of the surface radiator in such a higher-ranking device, in that the housing body can have, for example, one or several installation elements, such as fastening bores, tabs or collars.

A further advantageous embodiment of the surface radiator provides that the orifice opening is formed on a side of the fastening surface facing away from the inlet opening, i.e., lying spaced apart therefrom. The first cooling channel thereby runs through the housing body at least partly in a plane parallel to the fastening surface, in order to lead into the emission chamber in a region spaced apart from the inlet opening. Due to the fact that the first cooling channel extends through the housing body underneath the fastening surface, heat, which is generated by the LEDs and which is absorbed by the housing body via the fastening surface, can already be output from the housing body to the supplied coolant during the passage of the first cooling channel. The housing body is preferably made of a heat-conducting material, particularly preferably aluminum. The temperature of the housing body can also be kept constant in this way, so that the heat generated by the LEDs cannot only be dissipated on the front side by means of the direct contact of the LED with the coolant, but also on the rear side through the housing body to the coolant. The at least one discharge opening can preferably be formed on a side of the fastening surface, which is close to or faces the return opening, respectively, so that the second cooling channel, through which the heated coolant is guided to the return opening, can be kept as short as possible.

As a function of the number and/or performance of the LEDs, in particular in the case of a larger number and/or higher performance of the LEDs, it can be provided in a further embodiment of a surface radiator that the inlet opening is fluidically connected to a distributor channel section close to the inlet opening, from which several first cooling channels extend to the respective orifice openings through the housing body and parallel to the fastening surface. The second cooling channel can then extend from a collecting channel section, which is connected to a plurality of discharge openings, to the return opening. Alternatively, the first cooling channel can extend from the inlet opening to a distributor channel section spaced apart from the inlet opening, on which several orifice openings are formed, whereby the second cooling channel also extends here from a collecting channel section, which is connected to several discharge openings, to the return opening. In a possible, less preferred alternative, the housing body can have several first cooling channels with correspondingly several, in each case assigned inlet and orifice openings and several second cooling channels with correspondingly several, in each case assigned discharge and return openings.

According to a further embodiment, a surface radiator can have a holding frame, which is arranged, preferably releasably, on the housing body for holding the emission window and which is formed, corresponding to a window frame, for leaving the light opening provided by the emission window uncovered or free, respectively, for the at least one light-emitting semiconductor component. In order to seal the arrangement of holding frame and emission window on the housing body, a circumferential seal (e.g., by means of sealing strip in a corresponding sealing groove in holding frame and housing body) can be arranged between the holding frame and the emission window as well as between the emission window and the housing body.

Alternatively to the fastening of the emission window by means of holding frame, the emission window can, in a further embodiment, be fastened to the housing body by means of an adhesive layer, which simultaneously ensures the sealing. A virtually borderless embodiment of the surface radiator can advantageously be created hereby, which can be particularly well suitable for the integration into a higher-ranking device. An embodiment is further conceivable, which combines adhesive layer and holding frame when arranging the emission window on the housing body, for instance when the emission window is fixed in a sealing manner by means of an adhesive layer in a holding frame, which can be releasably arranged on the housing body, so that only a circumferential seal is required for sealing the holding frame or emission window, respectively, on the housing body.

A further embodiment of the surface radiator relates to the fact that on the front side, the housing body has at least one fastening ledge, which surrounds the fastening surface as stepped circumferential edge, wherein a first fastening ledge is formed for receiving the emission window, i.e., as support for the emission window. A route for the electromagnetic radiation through the coolant is defined by the height of the emission chamber thereby by the distance of the first fastening ledge, on which the emission window rests, from the fastening surface. One embodiment with a second fastening ledge, which surrounds the first fastening ledge as stepped circumferential edge, can be provided for the arrangement of a holding frame for fastening the emission window to the housing body.

In a preferred embodiment, the connecting opening can be connected to the connecting chamber via a passage opening, wherein a cross sectional surface of the passage opening is smaller than a cross sectional surface of the connecting opening, in order to simplify a sealing of the connecting opening with respect to the connecting chamber, which is filled with the coolant.

The passage opening can thereby have a cross sectional shape, which deviates from the circular shape, for example a polygonal shape or can, for example, be formed as dihedron, in order to provide for a rotation-restricted arrangement of a correspondingly formed connecting element, such as, e.g., of a connecting plug, which is connected to the connecting lines, or of an adapter element, through which the connecting lines extend.

In a further embodiment, a surface radiator can thus provide for the electrical connection that the at least one connecting line through the passage opening from the connecting chamber extends at least partially into the connecting opening or that the surface radiator has a connecting plug, which is connected to the at least one connecting line (optionally via a ballast), wherein the connecting plug extends at least partly into the connecting opening, optionally also into the passage opening leading to the connecting chamber. To avoid leakages through an insulating jacket of the connecting lines or of the connecting plug, the arrangement of the connecting plug (or of the connecting lines) in the connecting opening (and/or in the passage opening leading to the connecting chamber) can be sealed by means of a casting or solder compound.

According to one embodiment of a surface radiator, the surface radiator can further have an inlet connecting element, which is connected to the inlet opening for connecting a coolant supply line. The surface radiator further has a return connecting element, which is connected to the return opening for connecting a coolant return line. The connection of the inlet connecting element to the inlet opening and/or of the return connecting element to the return opening is thereby sealed by means of a casting or solder compound in order to avoid leakages.

A device for lighting, for carrying out a photochemical reaction or for disinfection has at least one surface radiator comprising at least one light-emitting semiconductor component, the emission spectrum of which provides a corresponding incident radiation for lighting, for carrying out a photochemical reaction or for disinfection.

According to a further embodiment of a device for lighting, for carrying out a photochemical reaction or for disinfection, the device has a housing. This is not only understood to be a wall, which completely surrounds a reaction chamber but also holders in a more general sense. The housing thus at least partly surrounds a lighting chamber, reaction chamber or disinfection chamber and has at least one installation space for the at least one surface radiator. The housing body of the surface radiator preferably has at least one installation element for the arrangement in the device at the predetermined installation space.

A use of a surface radiator is the lighting, carrying out a photochemical reaction or disinfection, wherein the at least one light-emitting semiconductor component of the surface radiator has an emission spectrum, which provides a corresponding incident radiation for lighting, for carrying out a photochemical reaction or for disinfection.

Further embodiments as well as some of the advantages, which are associated with these and further embodiments, become clear and better understandable by means of the following detailed description with reference to the accompanying figures. Objects or parts thereof, which are essentially identical or similar, can be provided with the same reference numerals. The figures are only a schematic illustration of an embodiment of the invention, in which:

BRIEF DESCRIPTION OF THE DRAWINGS

FIG. 5 shows a longitudinal sectional view through the surface radiator from FIG. 2 along cutting line DD, FIG. 6 shows a longitudinal sectional view according to FIG. 5 through the housing body, the emission window and the holding frame of the surface radiator in disassembled state, FIG. 7 shows a longitudinal sectional view through the surface radiator from FIG. 2 along cutting line EE, FIG. 8 shows a longitudinal sectional view through the surface radiator from FIG. 2 along cutting line FF.

DETAILED DESCRIPTION

The present disclosure relates to an LED surface radiator, which is predominantly provided as high-performance radiator for the industrial use, for example as surface radiator in a device for disinfecting surfaces or for carrying out a photochemical reaction. For this purpose, the surface radiator can be assembled, for example, in a holder above the surface, which is to be disinfected, or in a wall element of a photoreactor, which can also be a reactor cover. An LED surface radiator can further also be formed for lighting purposes or as heat radiator, which, as high-performance radiators, likewise require an effective heat dissipation. The present disclosure accordingly also relates to any device for lighting, as well as optionally to devices for the heat treatment, carrying out a photochemical reaction or disinfection, which has a surface radiator in an embodiment, as well as to the use of a surface radiator, in particular for lighting, but optionally also for the heat treatment, carrying out a photochemical reaction or disinfection in general.

Figure 9:
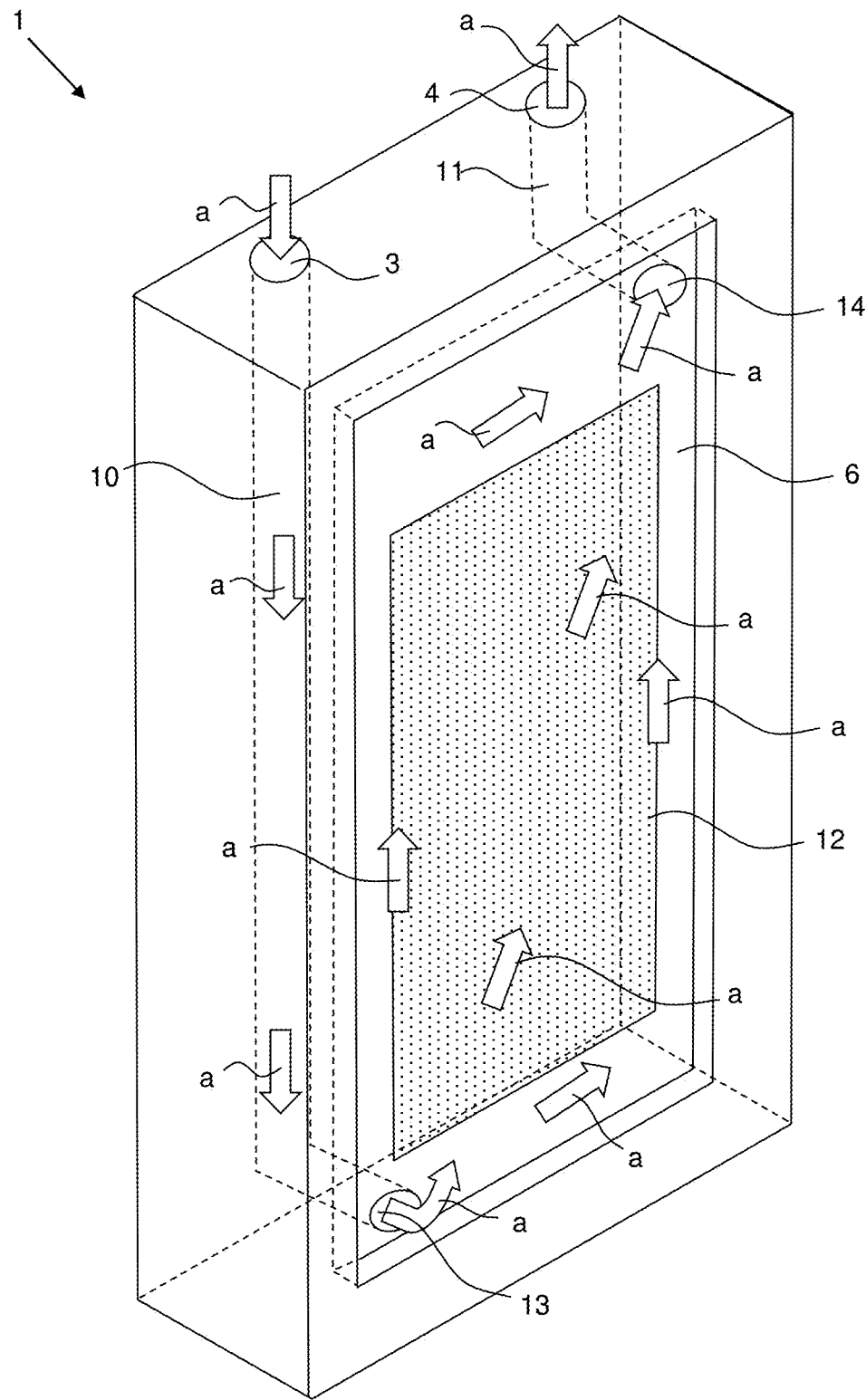
FIG. 9 shows a schematically perspective view of a housing body of a surface radiator with illustrated fluid path a, FIG. 10 shows a front view onto a surface radiator according to an embodiment comprising electrical connecting elements.
Figure 11:
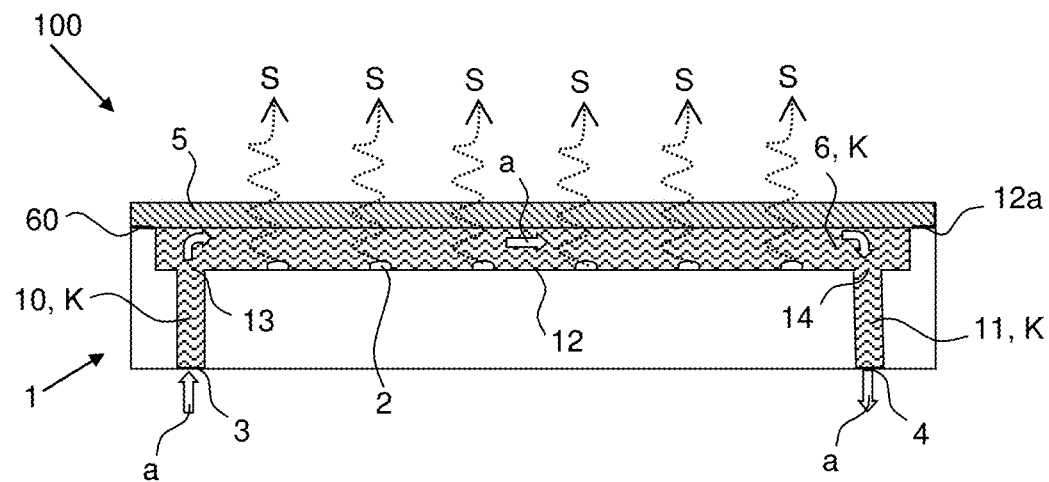
FIG. 11 shows a schematic longitudinal sectional view through a surface radiator according to a further embodiment.

The setup of a surface radiator 100 comprising many LEDs 2, which are arranged in a flat manner, and a housing body 1 is explained in FIGS. 1 to 8. FIGS. 9 and 11 with their simplified, low-detail schematic illustrations show the principle of the device and in particular the fluid path a of the coolant K through a surface radiator 100. The surface radiator 100 in FIG. 11 thereby has a different cooling channel design. In the surface radiator 100, the LEDs 2 arranged on a fastening surface 12 of the housing body 1 are overlaid by an emission window 5, which is arranged on the housing body 1 spaced apart from the fastening surface 12 and which is transparent for an incident radiation S emitted by the LEDs 2, which is suggested by the dotted wavy arrows in FIG. 11. The arrangement of the emission window 5 on the housing body 1 is thereby formed in a fluid-tight manner, so that the housing body 1, the LEDs 2 arranged on the fastening surface 12 and the emission window 5, which defines a front side of the surface radiator 100, delimit an emission chamber 6, through which the fluid path a runs. The emission chamber 6 is thus completely filled with the coolant K, which thus directly contacts the LED 2 for receiving and dissipating the generated heat. A heat-conductive and electrically insulating liquid is thus selected as coolant K, which, like the emission window 5, is transparent for the incident radiation S. In a surface radiator 100, the fluid path a thus runs in the flow direction of the coolant K, starting at an inlet opening 3, which is formed on an outer wall of the housing body 1, through a first cooling channel 10, which extends through the housing body 1 into the emission chamber 6 to an orifice opening 13, which is formed on a first side adjacent to the fastening surface 12. From the orifice opening 13, the fluid path a runs through the emission chamber 6 to a discharge opening 14, which is formed on a second side facing away from the first side next to the fastening surface 12 and which connects the emission chamber 6 to a second cooling channel 11, which leads through the housing body 1 to a return opening 4 on an outer wall of the housing body 1.

Due to the direct contact, the coolant K, which fills and flows through the emission chamber 6, effectively dissipates a significant portion of the heat generated by the LEDs 2 during operation. The housing body 1 can additionally be made of a heat-conductive material, which can in particular be a metal material and particularly preferably aluminum or an aluminum alloy, so that a certain portion of the heat generated by the LEDs 2 can also be dissipated on the rear side of the LED 2 to the housing body 1.

The heat absorbed by the coolant K can preferably be cooled down after discharge through the return opening 4 outside of the emission chamber 6 or outside of the housing body 1, respectively, and the cooled-down coolant K can be supplied again by in circulation via the inlet opening 3. The surface radiator 100 can thus have corresponding known elements for forming a coolant circuit. The coolant K, which fills and flows through the emission chamber 6, further also ensures a thermal decoupling of the LED 2 from the surrounding area adjoining the emission window 5, in that the coolant K can also exchange heat with the surrounding area via the emission window 5. The coolant K filling the emission chamber 6 further advantageously ensures an avoidance of near-field reflection between LEDs 2 and emission window 5 and prevents the occurrence of volatile organic hydrocarbon compounds (VOCs) in the emission chamber 6, which could damage the LED 2. By filling the emission chamber 6 with the coolant, an explosive atmosphere is further avoided. A surface radiator 100 is thus not only improved with respect to the cooling of the LEDs 2 and the thermal decoupling thereof from the surrounding area but additionally protects the LEDs 2 against harmful substances and furthermore provides an increased total light or radiation performance, respectively, of the incident radiation S with regard to the prior art in a particularly advantageous manner. This results from the fact that the volatile coolant K, which is preferably selected from saturated hydrocarbons, silicone oils and synthetic ester and ether compounds and the index of refraction of which is significantly larger than that of air or inert gas and which lies in the range of approximately 1.35 to approximately 1.55 (at 20° C.) for suitable cooling liquids, increases the photon decoupling efficiency at the phase boundary of the diode surface to the coolant K in the emission chamber 6. The reflection at the phase boundary between the coolant K in the emission chamber 6 and the emission window 5 is decreased thereby.

The incident radiation for a predetermined use of the surface radiator, e.g. for lighting, carrying out a photochemical reaction or for disinfection is provided by means of LEDs, the doping of which ensures electromagnetic radiation with the wavelength(s) provided for the use. As is well known, LEDs are available, which do not only cover the visible light ranges but also infrared and/or UV spectral ranges. The material selection of the emission window and of the coolant can thus be limited by the wavelength range of the incident light. For the lighting, the incident radiation is thus visible light, so that the emission window is transparent at least for the portion of the electromagnetic spectrum with wavelengths of approx. 380 to 780 nm. UV radiation (100-380 nm) can be used as incident radiation for disinfection and for carrying out photochemical reactions, so that the emission window is in each case made of a material, which is transparent at least for the used UV wavelengths. UV-C radiation (100-280 nm) is thus used for disinfection purposes. UV-B (280-315 nm) and UV-A radiation (315-380 nm) is used for many photochemical reactions, without photochemical reactions being limited to this spectral range because the incident radiation required for carrying out photochemical reactions is a function of the type of the intended reaction of an absorption wavelength of a starting product, so that the incident radiation for certain photochemical reactions can optionally also in the other wavelength ranges.

The emission window can generally also be transparent for wavelengths other than those of the incident radiation, but it can also be desirable—in particular in the field of photochemical reactions—that the emission window should be transparent only for certain wavelengths, so that the emission window—due to material or a coating—can also take over a filter function in order to filter out undesirable wavelengths. The selection of the window material, for example from different glass and plastic materials, as a function of the wavelengths of the incident radiation is a customary task. The person of skill in the art thus knows that, e.g., synthetic quartz and borosilicate glasses containing large quantities of boron still have a good transparency even in the UV-C range. In the infrared spectral range, glass ceramics further display good transparency and can be used as window material there. If the intended use is carrying out a photochemical reaction, it is important to note when selecting a window material that no reactions take place with the reactants or products. The coolant is accordingly selected from electrically insulating liquids as a function of the spectral range of the respective incident radiation. Window materials and cooling liquids are considered to be "transparent" when they have a transmission degree of at least 75% each for the wavelength(s) of the incident radiation along the respective route through the emission window or through the emission chamber, respectively, between LED surface and emission window.

The liquid coolant for incident radiation in the visible and UV spectral range can be selected, for example, from highly refined mineral oils, which virtually comprise only alkanes and cycloalkanes, thus saturated hydrocarbons. Advantageously, alkanes and cycloalkanes are transparent from the visible wavelength range all the way into the wide UV-C range (220-230 nm). Below this, the transmission decreases, but can still be sufficient for wavelengths of up to 195 nm and below, in particular in the case of a sufficiently small route between LED and emission window. Compared to the correspond linear alkane, cycloalkanes can be preferred due to the higher index of refraction. The indices of refraction (20° C.) for $C_5$-$C_{14}$ cycloalkanes thus extend over a range of approximately 1.41 to 1.55, while the indices of refraction (20° C.) for the corresponding linear $C_5$-$C_{14}$ alkanes cover a range of approximately 1.36 to approximately 1.43. Cyclohexane, for example, has an index of refraction of approximately 1.43, while hexane has an index of refraction of approximately 1.37. In particular the formation of highly flammable steam-air mixtures with a classification in temperature class 3, which specifies a maximum surface temperature of 200° C. for the operation in flammable atmospheres, is a disadvantage of the saturated hydrocarbons. When using highly refined mineral oils as coolant, it is thus important to pay attention to a careful and sealed exclusion of air in order to avoid the formation of such flammable steam-air mixtures.

A preferred embodiment can provide low-viscosity silicone oils, which have indices of refraction in the range of approximately 1.37 to 1.40, are advantageously not combustible and which are transparent from the visible wavelength range all the way into the medium UV-C range (approximately 250 nm) as coolant for incident radiation in the visible and UV spectral range. Below 250 nm, however, the transmission starts to decrease and wavelengths of less than 200 nm are absorbed, so that silicone oils are suitable in particular for areas of application, which want to use wavelengths of larger than 250 nm. Silicone oils are only suitable to a limited extent for applications, which want to utilize wavelengths in the range of 200 to 250 nm, namely when the route in the emission chamber between LED and emission window and thus the absorption is small enough to allow for a sufficient transmission. Saturated hydrocarbons as coolant should otherwise be used in the spectral range below 250 nm.

Further alternative examples for coolants which can be used in the visible and UV spectral range comprise synthetic ester and ether compounds. Compared to the mineral oils, synthetic organic ester oils have the advantage of, for example, a higher temperature resistance and higher combustion and ignition temperature and are more environmentally friendly, but have a smaller resistance to aging and are transparent all the way into the medium UV range (approximately 270 to 280 nm), below that the absorption increases significantly. In the case of ether compounds, such as, for example, 1,4-dioxane with an index of refraction of 1.422, the transmission also reaches all the way into the medium UV range (270 to 300 nm, aside from diethyl ether up to 255 nm), but the transmission below that decreases less steeply, so that ether compounds can also be used as coolant for wavelengths of below 270 nm in the case of a sufficiently small route between LED and emission window. Wavelengths smaller than 220 nm, however, are absorbed. With regard to the safety technology, however, it is important to take into account that ether compounds form easily flammable steam-air mixtures, whereby there are large differences between the different ether compounds. Diethyl ether, for example, falls within temperature class T4 (maximally permissible surface temperature 135° C.), while 1,4-dioxane falls within temperature class 2 (maximally permissible surface temperature 300° C.), so that 1,4-dioxane can be used more easily as coolant.

Depending on the wavelength of the incident radiation, fluorinated hydrocarbons, such as perfluorohydrocarbons and hydrofluoroethers, can optionally also be used as coolant, which are advantageously not combustible but have absorption bands in certain wavelength ranges: if the incident radiation lies outside of the absorption bands, fluorinated hydrocarbons, such as, for example, 3M Fluorinated Electronic Liquid or 3M Novec High-Tech liquid by 3M™ (3M electronics, St. Paul, USA) can be used. It goes without saying that further liquids can also be used as coolant in a surface radiator, as long as they are electrically insulating and transparent for the wavelength of the incident radiation. In order to provide a transmission of at least 75%, which is required for the desired transparency, the distance of the emission window from the fastening surface with the LEDs can be minimized, if possible, so that the route through the emission chamber, which is filled with coolant, between LED and emission window—and thus the absorption of the incident radiation is decreased accordingly. During the dimensioning of the emission chamber with respect to the distance of the emission chamber from the fastening surface comprising the LEDs, the conditions for an optimal flow guidance in connection with a sufficient liquid volume are to be taken into account at the same time for an optimal heat dissipation.

In a preferred embodiment of the surface radiator 100, the first cooling channel 10 extends through the housing body 1 in a way that the orifice opening(s) 13 are formed next to the fastening surface 12 on a side, which is spaced apart from the inlet opening 3, as can be seen in FIGS. 1 to 10 and 12 to 14, so that the first cooling channel 10 runs through the housing body 1 at least partly in a plane parallel to the fastening surface 12. The coolant K flowing through the first cooling channel 10 can already absorb a heat portion dissipated from the LEDs 2 via the housing body 1 during the passage of the first cooling channel 10 in this way, before the coolant K flows into and through the emission chamber 6, in order to dissipate the main portion of heat from the LEDs 2 by means of direct contact. The design of the first cooling channel 10 (distance from the fastening surface 12 and course underneath the fastening surface 12) and an adapted coolant flow rate can ensure that a temperature rise of the coolant through the passage of the first cooling channel 10 is small. The second cooling channel 11, which leads to the discharge opening 14 and through which the coolant K flows, which was heated due to the passage of the emission chamber 6, is kept as short as possible, in order to minimize the heat transfer at the housing body 1. The discharge opening 14 in the shown examples is thus formed on a side of the fastening surface 12 close to the return opening 4.

In the examples of FIGS. 1 to 11, the respective surface radiator 100 has a first coolant channel 10, which leads from an inlet opening 3 to an orifice opening 13, and a second coolant channel 11, which connects the discharge opening 14 to the return opening 4. This simple embodiment can in fact be sufficient for the effective cooling of the LED 2—depending on the size of the surface radiator 100, i.e., number and distribution of the LEDs 2 at the fastening surface 12 as well as the line thereof. The orifice opening 13 and the discharge opening 14 are thereby not only arranged on opposite sides of the fastening surface 12, but are also assigned to diagonal corners of the fastening surface 12, in order to flow as evenly as possible past all LEDs 2, if possible.

Figure 12:
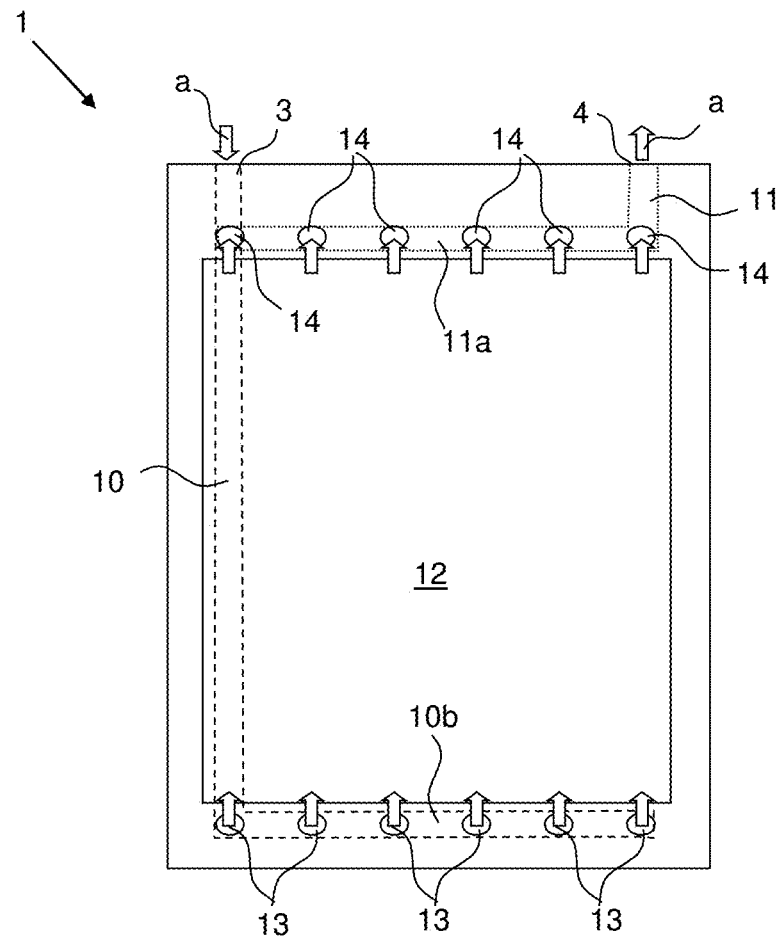
FIG. 12 shows a schematic front view onto a surface radiator comprising a distributor channel close to the orifice opening according to a further embodiment.
Figure 13:
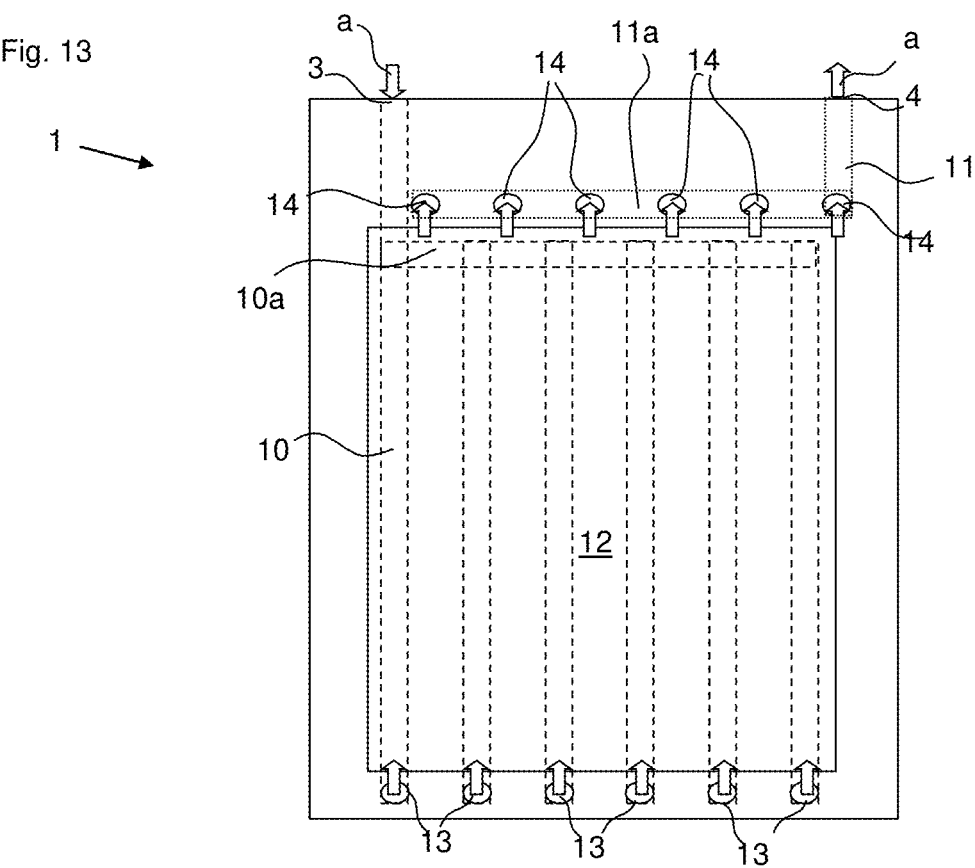
FIG. 13 shows a schematic front view onto a surface radiator comprising a distributor channel spaced apart from the orifice opening according to a further embodiment.
Figure 14:
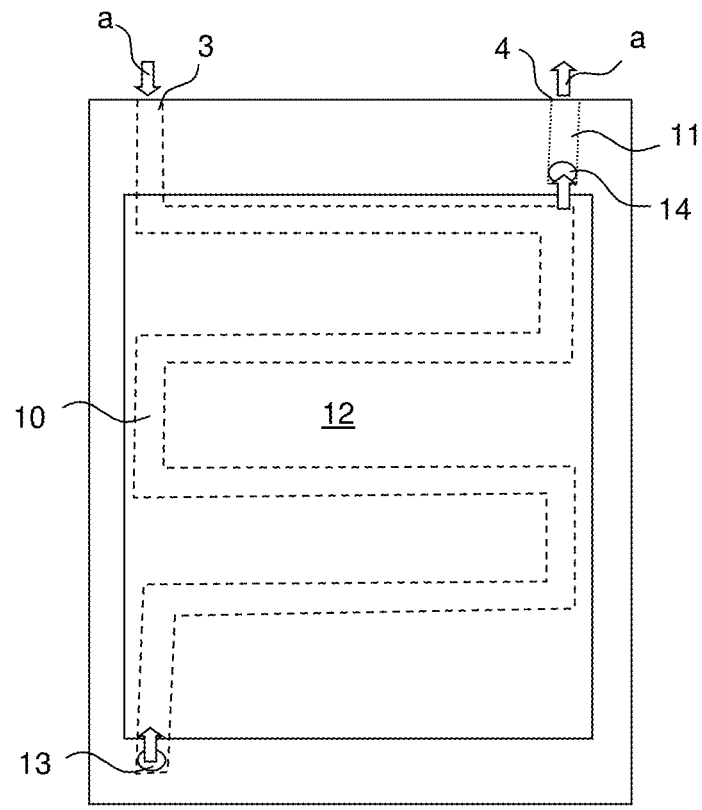
FIG. 14 shows a schematic front view onto a surface radiator comprising a meandering first cooling channel according to a further embodiment.

For the further equalization of the coolant flow through the emission chamber 6, several orifice and discharge openings 13, 14, which are arranged so as to be distributed evenly along the respective side, can in each case be provided on the sides of the fastening surface 12 facing away from one another, as shown in FIGS. 12 and 13. The schematic illustrations are to only clarify the respective principle, but are not true to scale and do not represent a limitation with respect to the number and arrangement of the openings as well as course and diameter ratios of the channels. FIG. 12 clarifies a variation, in the case of which the first cooling channel 10 runs through the housing body 1 from the inlet opening 3 to a distributor channel section 10b, which, based on the fastening surface 12, extends in the housing body 1 along a side, which lies spaced apart or facing away from the inlet 3, respectively. The distributor channel section 10b is connected to a plurality of orifice openings 13, which are formed next to the fastening surface 12 on the side spaced apart from the inlet. On the other side of the fastening surface 12 close to the inlet, a corresponding plurality of discharge openings 14 is formed, which are connected via a collecting channel section 11a to the second cooling channel 11, which extends to the return opening 4.

In a modified, non-illustrated variation, the housing body 1 can have several parallel first cooling channels 10, each of which extends from a respective assigned inlet opening 3 to a correspondingly assigned orifice opening 13. The housing body 1 can accordingly have several second cooling channels 11, each of which extends from a respective assigned discharge opening 14 to a respective assigned return opening 4. This embodiment is less preferred because several inlet and return connections are required for the coolant. A design of the fluid path a with the several cooling channels can nonetheless be expedient for certain embodiments of the surface radiator 100 as a function of the number, arrangement and performance of the used LED 2.

FIG. 13 shows a design of the fluid path a similarly as in FIG. 12, but with the difference that with respect to the fastening surface 12, the distributor channel section 10a is formed here on a side close to the inlet, i.e., spaced apart from the orifice opening, so that several first cooling channels 10 extend parallel to the fastening surface 12 from the distributor channel section 10a through the housing body 1 to the respectively assigned orifice openings 13. By means of the arrangement of several first cooling channels 10, which extend underneath the fastening surface 12 parallel thereto to the orifice openings 13, a more even temperature control of the housing body 1 can be attained, if required, during the passage of the first cooling channels by the coolant than in the case of a single first cooling channel 10, which runs in a straight line on one side underneath the fastening surface 12. However, a more even temperature control can also be attained with only one cooling channel 10, when the latter has a course, which evenly covers the fastening surface 12, such as, for example, the meandering course in FIG. 14. While the simpler cooling channel designs of the examples from FIGS. 1 to 11 with maximally one change in direction of the cooling channel section can be manufactured by means of one- or two-sided bores in the housing body 1, the more complex cooling channel designs with more than one change in direction of the channel sections require multi-sided bores comprising following closures of the bore sections, which do not belong to the fluid path or optionally a generative manufacturing method of the housing body.

For the fluid-tight arrangement of the emission window 5 on the housing body 1, in order to seal the emission chamber 6, which is filled with coolant K, against the surrounding area, a holding frame 17 is provided in the case of the exemplary surface radiator 100 shown in FIGS. 1 to 10, which, in this example, is releasably fastened to the housing body 1 by means of screws 50, for which corresponding fastening bores 19 are provided in the holding frame 17 as well as in the housing body 1. The holding frame 17 delimits an opening 17a, the surface dimensioning of which essentially corresponds to the fastening surface 12, in order to leave the LED 2 uncovered and to allow the radiation exit through the emission window 5. The sealing of the emission chamber 6 thereby takes place by means of the arrangement of a respective circumferential seal 18 between the holding frame 17 and the emission window 5 as well as between the emission window 5 and the housing body 1, for the purpose of which the holding frame 17 and the housing body 1 each have corresponding sealing grooves 18a (identified in FIG. 6) for receiving a sealing strip or of a corresponding sealing element.

The surface radiator 100 from the example of FIG. 11 forgoes a holding frame, in that the emission window 5 is fastened to the housing body 1 by means of an adhesive layer 60 and is sealed simultaneously. The surface radiator 100 is thus embodied in a virtually borderless manner and is thus particularly suitable for the seamless installation into a reactor wall element of a device for carrying out a photochemical reaction, for example.

It goes without saying that variations and combinations of the fastening and sealing of an emission window to a housing body are also conceivable, such as, e.g., that an emission window is fastened and sealed by means of an adhesive layer to a holding frame, which is releasably fastened to the housing body, wherein the arrangement of the holding frame on the housing body is sealed by means of a sealing means.

If a use of a surface radiator is provided in a device for carrying out a photochemical reaction, the sealing of the emission window on the housing body with respect to material selection and shaping is designed according to the provided reaction pressures and reaction temperatures, which can prevail in the reaction chamber adjoining the emission window. This includes in particular reaction temperatures and pressures deviating from room temperature and ambient pressure, which prevail in the reaction chamber adjoining the emission window and which can also comprise temperatures of below +5° C. and above +40° C. as well as pressures in the range of high vacuum and overpressure of 6 bar.

As can be seen particularly well in FIG. 6, the housing body 1 of the shown exemplary embodiment of a surface radiator 100 has a first fastening ledge 12a for the arrangement of the emission window 5 and a second fastening ledge 12b for the arrangement of the holding frame 17, which surround the fastening surface 12 in a stepwise manner. The first fastening ledge 12a is thereby bordered by the stepping of the second fastening ledge 12b, wherein the dimensions of the bordered surface corresponds to the emission window 5, which is to be arranged, and the height of the stepping to the second ledge 12b corresponds to the thickness of the emission window 5. The height of the stepping of the first fastening ledge 12a with regard to the fastening surface 12 determines the distance of the emission window 5 from the fastening surface 12 and thus the height of the emission chamber 6, which defines the route for the radiation emitted by the LEDs 2 through the coolant K. The second fastening ledge 12b for the holding frame 17 is also delimited by a border web, wherein the dimensions of the surface bordered thereby and the height of the border web correspond to the respective dimensions of the holding frame 17, which is to be arranged.

The housing body 1 of the example from FIG. 11, in the case of which the emission window 5 is fastened to the housing body 1 by means of an adhesive layer 60, also has a first fastening ledge 12a, but without being bordered by a further fastening ledge or web, so that the emission window 5 covers the front side of the housing body 1 in a flat manner. Deviating from the illustrated example, a bordering of the first fastening ledge 12a can also be provided by means of a further ledge or web for the arrangement of an emission window fastened by means of adhesive layer, wherein the dimensions of the surface bordered thereby and a height of the border web correspond to the respective dimensions of the emission window.

To accommodate electrical connecting elements for the LEDs 2, the surface radiator 100 of the examples from FIGS. 1 to 8 and 10 has, on the front side in the housing body 1 adjacent to the fastening surface 12, a connecting chamber 15, which is formed in the housing body 1 between the first and the second cooling channel 10, 11, open to the emission chamber 5. In the illustrated example, the connecting chamber 15 is covered by means of the holding frame 17, which, for this purpose, has a wider frame section on the corresponding side. A connecting opening 16b, which allows for an electrical connection to an energy source, is formed in the housing body 1 by means of the connecting chamber 15 via a passage opening 16a. In the example illustrated in FIG. 10, the electrical connecting elements, which extend into the connecting chamber 15, comprise connecting lines 22 for connecting the LEDs 2.

In the case of the illustrated exemplary surface radiator 100, the light-emitting semiconductor components 2 are arranged on a printed circuit board 20, which, for connecting the LEDs 2, has corresponding conductor tracks (not illustrated), which lead to connecting contacts 21, which are arranged on a side of the printed circuit board 20 close to the connecting chamber 15. A pair of connecting contacts 21 is in each case provided for each row of LED 2 and is connected to a respective connecting line 22. As in the example of FIGS. 1 to 8, the printed circuit board 20 can be fastened by means of screws 50 to the fastening surface 12 of the housing body 1, which has corresponding fastening bores 19 for this purpose.

As outlined in FIG. 11, however, the LEDs 2 can also be fastened individually to the fastening surface 12 without printed circuit board 20. Each LED 2 can then have its own connection, wherein such an embodiment is possible in particular for a surface radiator 100 with a limited number of LEDs or for a surface radiator 100, in the case of which the LEDs are arranged in a single row, which allows for a lateral connection of each LED. In the case of a surface radiator with several rows of LEDs, it can be provided, for example, when forgoing a printed circuit board 20, which has conductor tracks for the electrical connection of the LEDs, that the fastening surface has slits. The slits are incorporated in the fastening surface so that connecting lines to the respective LEDs can run therein and shadings of the LEDs due to the connecting lines thus do not occur. The individual connection of the LEDs, which can thus be controlled individually, makes it possible that, when one LED fails, only the affected and not all LEDs have to be turned off, so that the remaining LEDs still remain in operation.

Figure 15:
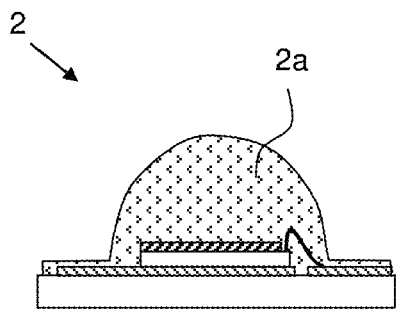
FIG. 15 shows a schematic cross sectional view through an LED comprising primary optics, which can be used as light-emitting semiconductor component in a surface radiator.
Figure 16:
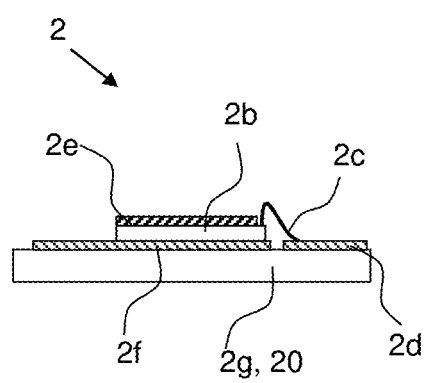
FIG. 16 shows a schematic cross sectional view through a primary optics-free LED, which can be used as light-emitting semiconductor component in a surface radiator according to a further embodiment.

A conventional LED 2 comprising a plastic lens as primary optics 2a is illustrated in FIG. 15, which can be used in an LED surface radiator 100. By means of the flooding with coolant, in contrast to the use of an inert gas, such as nitrogen, it is advantageous that an accelerated aging of the primary optics 2a of the LED 2 is avoided because VOCs ("volatile organic compounds"), which penetrate into the primary optics 2a, which is usually embodied as silicone lens, cloud it and thus lower the light yield, are present in particular in chemical plants. Due to the fact that the primary optics 2a are no longer exposed to a gaseous atmosphere but are shielded by the coolant, the aging process is slowed down significantly. In order to completely avoid the limitations in the light yield as a result of the aging process of the primary optics 2a, it is advantageously possible in the case of a surface radiator 100 that the LED 2 of the surface radiator 100 completely forgoes the primary optics 2a, such as silicone lenses because the semiconductor chip of the LED is already sufficiently protected against environmental influences due to the liquid coolant, and the coolant takes over the functions of the primary optics. FIG. 16 shows an LED 2, which is free from primary optics, the setup of which with semiconductor crystal 2b, wire 2c, anode 2d, LED chip 2e, cathode 2f and base structure 2g or printed circuit board 20, respectively, can otherwise correspond to the conventional LED 2 from FIG. 15, in the case of which, aside from saving a component, the cooling effect is further improved in an advantageous manner.

Figure 10:
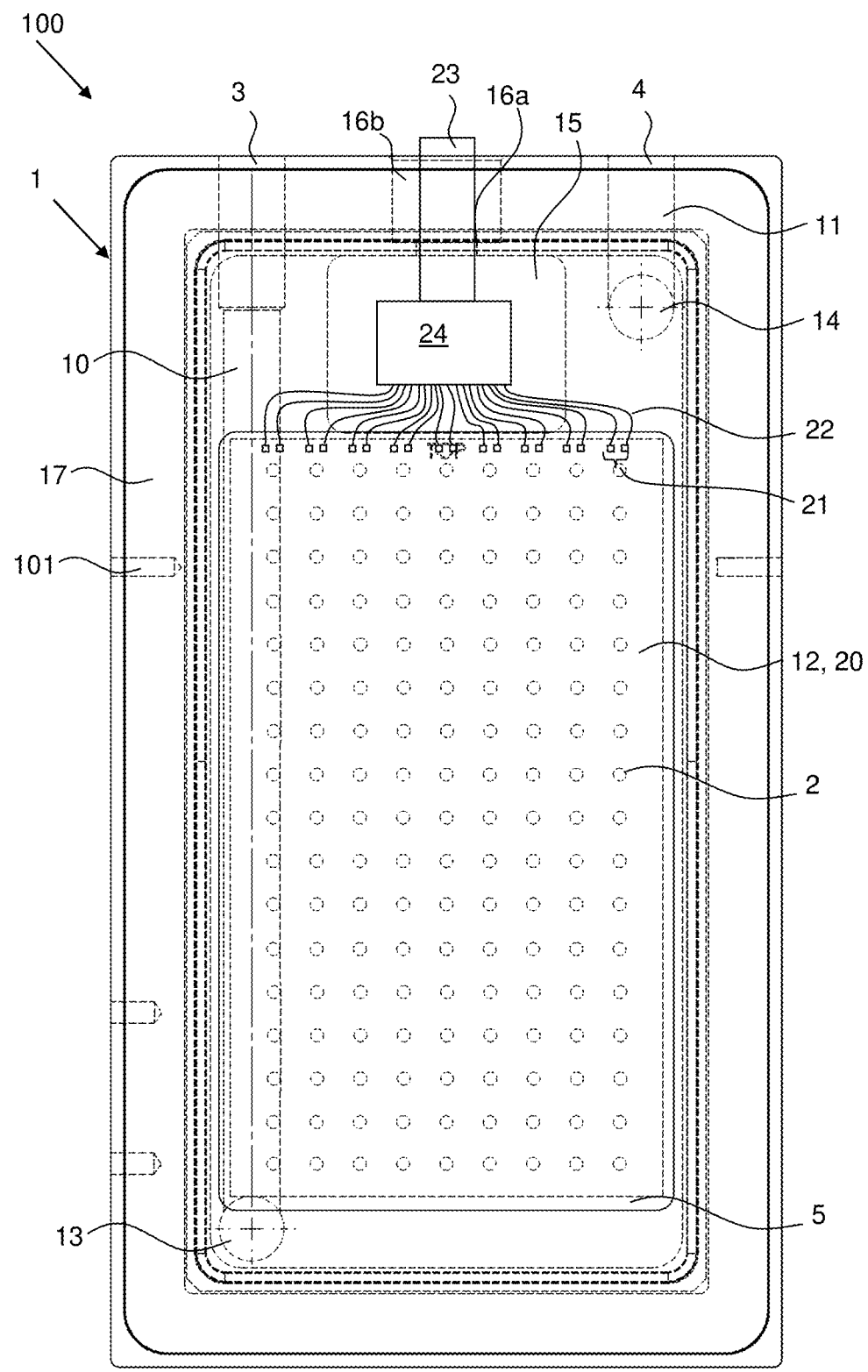

As can be seen in FIG. 10, a ballast 24 for the LEDs 2, which is connected to the connecting line 22, can further be accommodated in the connecting chamber 15. Due to the fluidic connection of the connecting chamber 15 to the emission chamber 6, the connecting chamber 15 is likewise filled with coolant and can also dissipate the heat generated by the ballast 24 during operation. An arrangement of the ballast 24 on the printed circuit board 20 can thus be forgone, whereby a heat input through the ballast 24 via the printed circuit board 20 on the adjacent LEDs 2 is avoided. An arrangement of a ballast 24 on a printed circuit board 20 in a surface radiator 100, is not ruled out, however, because the coolant also ensures an effective heat dissipation in such an embodiment. In a non-illustrated alternative, ballasts, such as DC converters or also power supply units can further be assembled in a housing attachment on the rear side of the housing body. The liquid coolant can also be used here for cooling the DC converters or other ballasts by connecting the housing attachment to the cooling circuit. For the safe operation with ATEX certification, an inertization, a pressure-resistant design or an oil encapsulation of this rear-side housing attachment can be realized. A further, non-illustrated alternative can provide the arrangement of the ballast outside of the connecting chamber and of the emission chamber, so that only the connecting lines 22 are located in the connecting chamber 15 and can extend to the or through the connecting opening 16b. This means that electrical or electronic devices, such as DC converters or other ballasts can optionally also be stored in a separate housing in the vicinity of the surface radiator housing body. In the event that the surface radiator 100 is operated in an ex-classified zone, the separate housing can then be assembled outside of the ex-classified zone.

Figure 1:
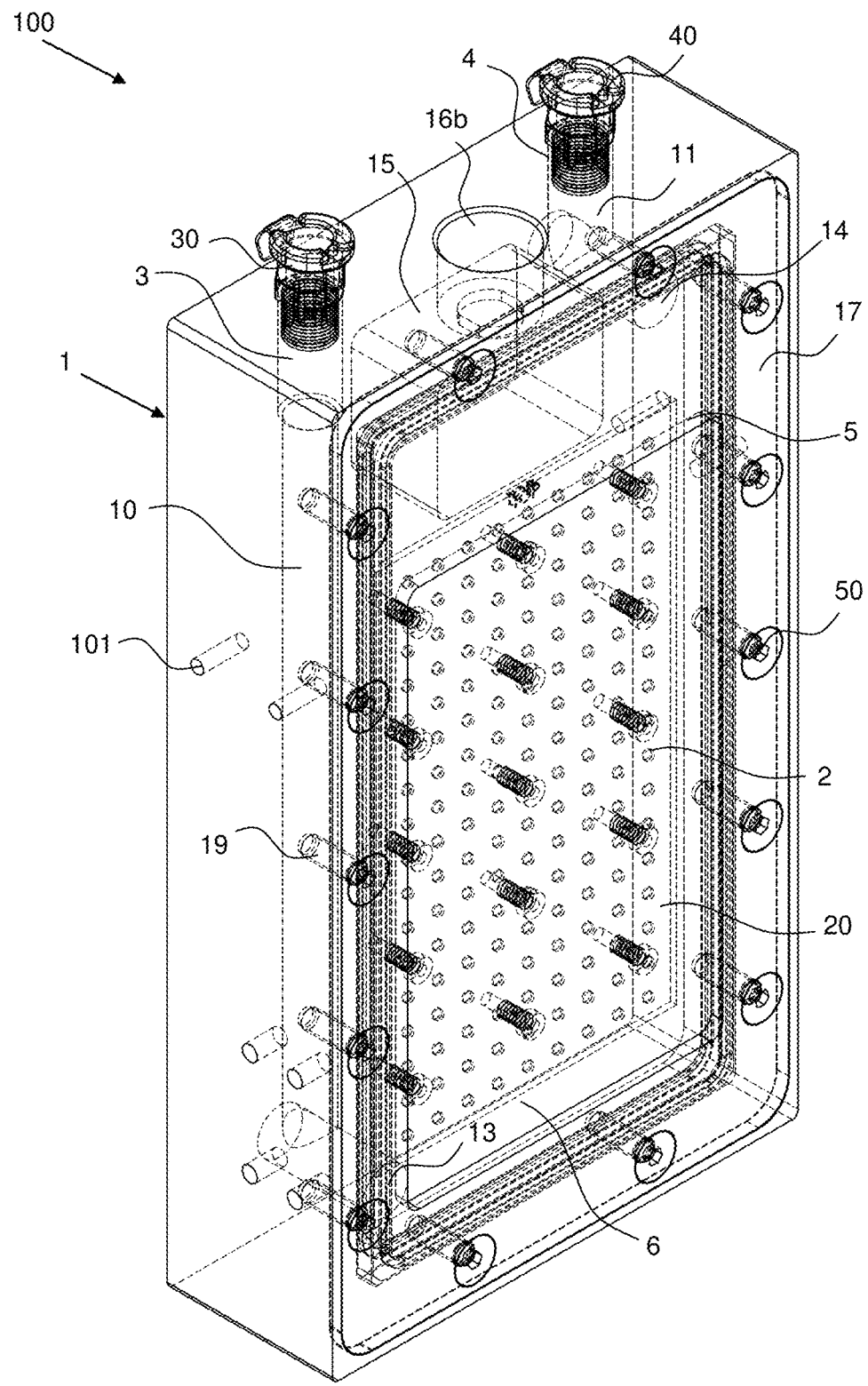
FIG. 1 shows a perspective view of the surface radiator.
Figure 2:
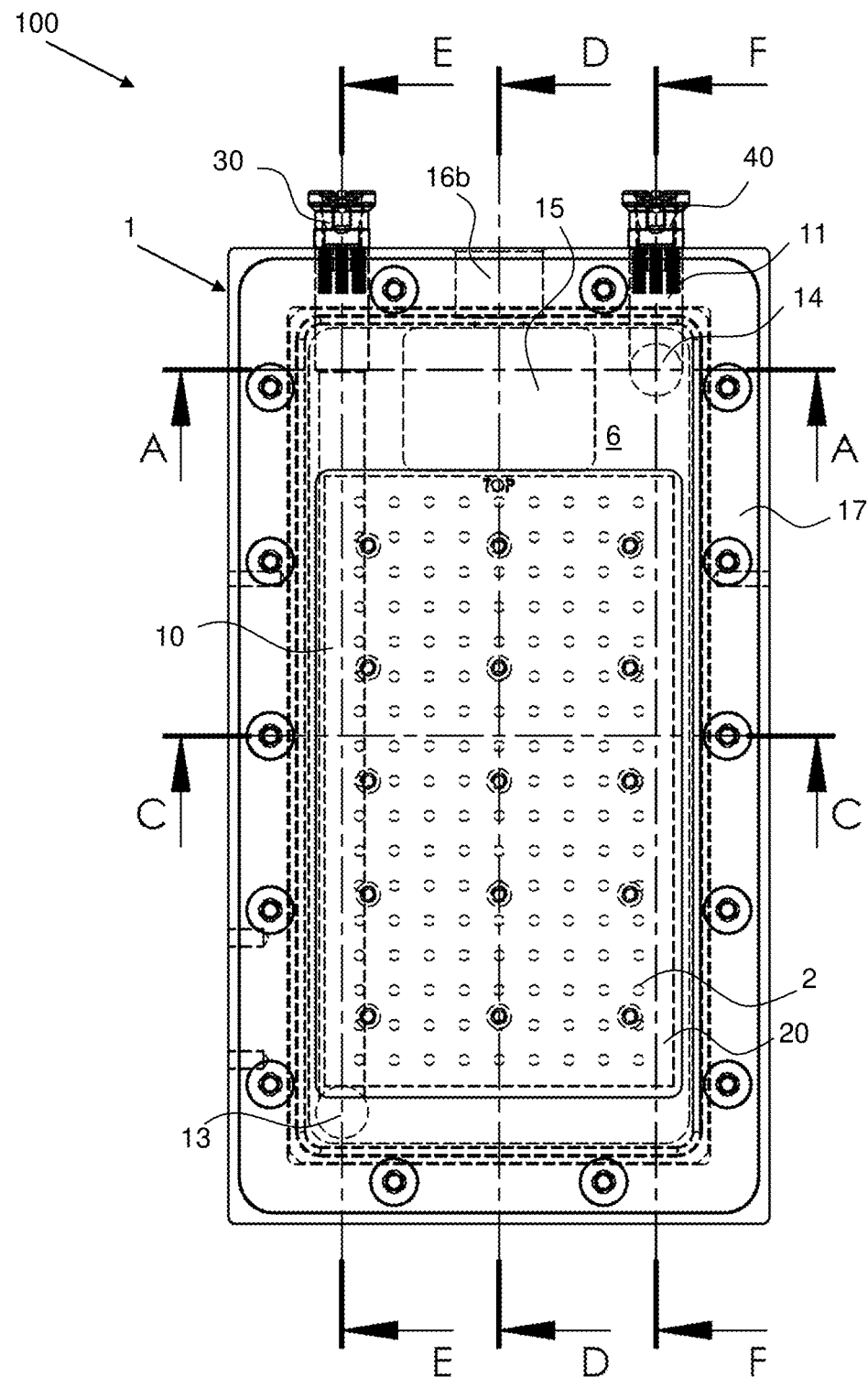
FIG. 2 shows a front view onto the surface radiator from FIG. 1 with the cutting lines AA, CC, DD, EE, FF.
Figure 3:
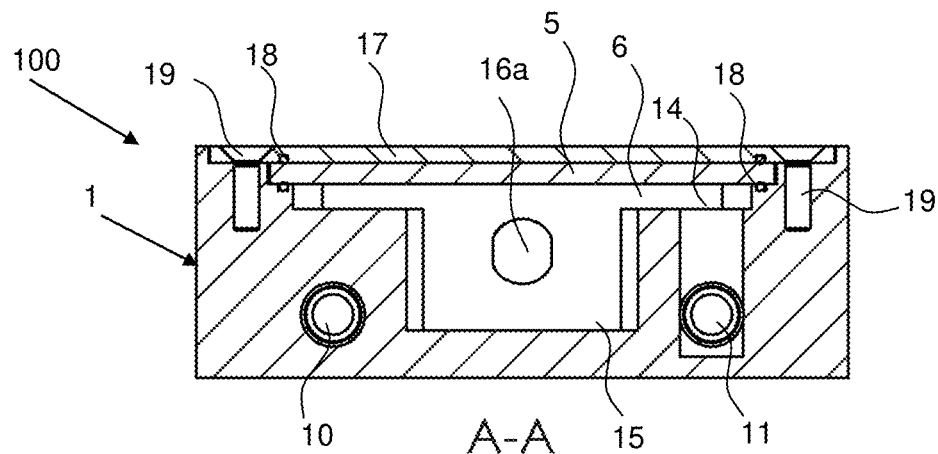
FIG. 3 shows a cross sectional view through the surface radiator from FIG. 2 along cutting line AA.
Figure 4:
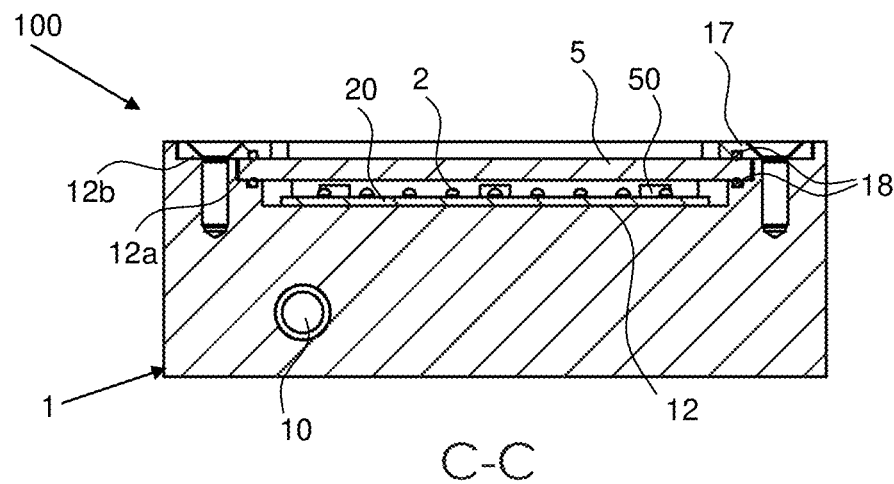
FIG. 4 shows a cross sectional view through the surface radiator from FIG. 2 along cutting line CC.

A connecting plug 23, which is connected to the ballast 24 in FIG. 10, but which can alternatively also be connected to connecting lines 22, extends from the connecting chamber 15 through the passage opening 16a, the cross sectional surface of which is smaller than that of the connecting opening 16b, and through the connecting opening 16b, so that the electrical connection of the surface radiator 100 can take place from the outside. The connecting plug 23 can thereby have a section, the cross section of which corresponds to the cross sectional surface of the passage opening 16a, which, as can be seen in FIG. 3, can deviate from the circular shape and which is formed as dihedron in the example illustrated there. Contrary to the illustration in FIG. 10, a connecting plug 23 can have a stepped shape, so that the connecting plug 23 does not only have a section, which is adapted to the cross section of the passage opening 16a, but also a section, which is adapted to the cross section of the connecting opening 16b, in order to seal the connecting chamber 15. Alternatively or additionally, a casting or solder compound can be used for sealing the arrangement of the connecting plug 23 in the connecting opening 16b and/or in the passage opening 16a, in order to avoid leakages by means of the insulation of the connecting plug 23. The same applies for embodiments, in the case of which the arrangement with connecting lines 22 or with a cable comprising the connecting lines 22, which extend through the passage opening 16a and the connecting opening 16b, is to be sealed in order to avoid leakages of the coolant from the connecting chamber 15, so that no coolant can pass to the outside through the insulation or the shielding of the electrical lines due to capillary effects.

The arrangement of an inlet connecting element 30, which is arranged in inlet opening 3 formed in the housing body 1 and thus provides the inlet connection of the surface radiator 100, and of a return connecting element 40, which is arranged in the return opening 4 formed in the housing body 1 and thus provides the return connection of the surface radiator 100 (see FIG. 1, 2, 5, 7, 8), can also be sealed against leakages in a similar way by means of a casting or solder compound.

All connecting points can generally be embodied in a fluid-tight manner, in order to prevent that coolant can pass to the outside of the surface radiator 100 due to capillary effects along the respective connecting elements. Measures, such as, for example, the casting of line sections into the housing body 1 and/or plug connections sealed by means of seals can optionally be sufficient for this purpose. All electrical connections, which are surrounded by the coolant or come into contact therewith, can further be embodied in a fluid-tight manner, in order to avoid that the coolant penetrates between contacting points, for example, as a result of creeping and capillary effects due to the surface tension, where the electrical contact could possibly be impaired or interrupted. In the case of plug connections, sealed plugs could possibly be sufficient, but further measures, e.g., a soldering of the contact points, are optionally also required, so as to not only avoid a creeping of the coolant but to also ensure the electrical contact.

Figure 17:
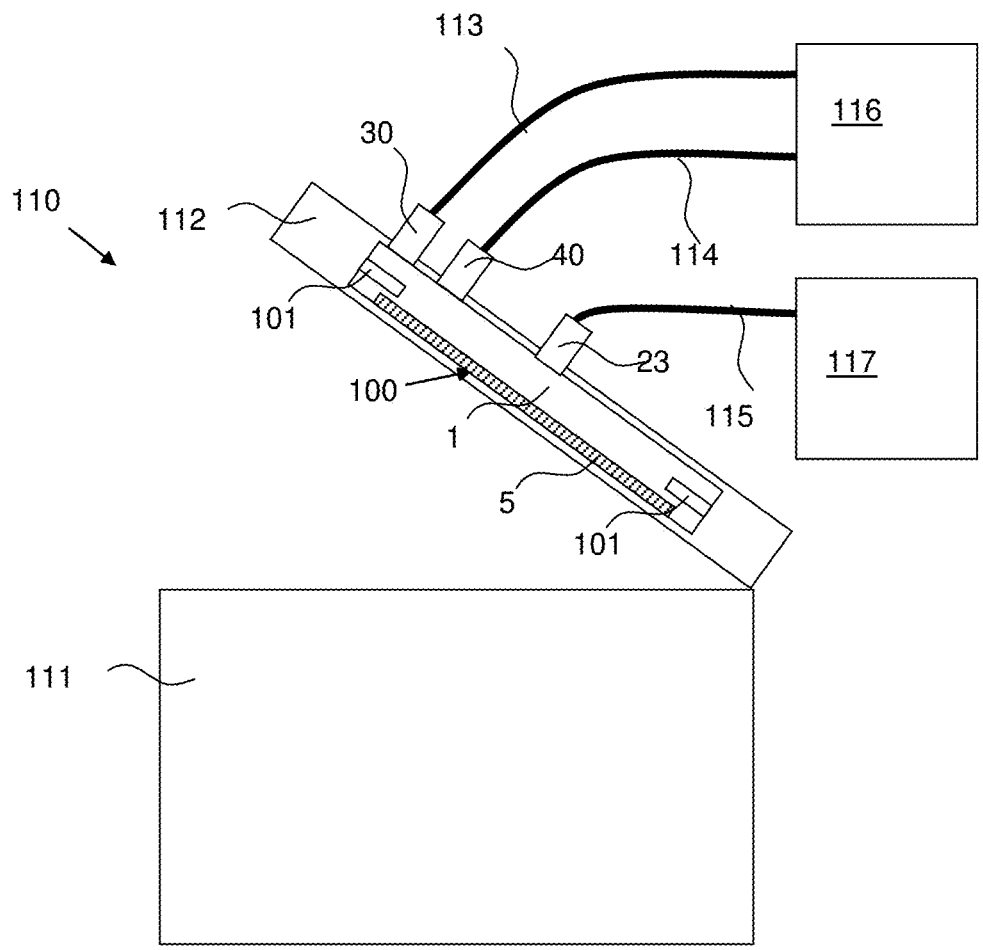
FIG. 17 shows a schematic side view onto a device according to an embodiment having a surface radiator for carrying out a photochemical reaction.
Figure 18:
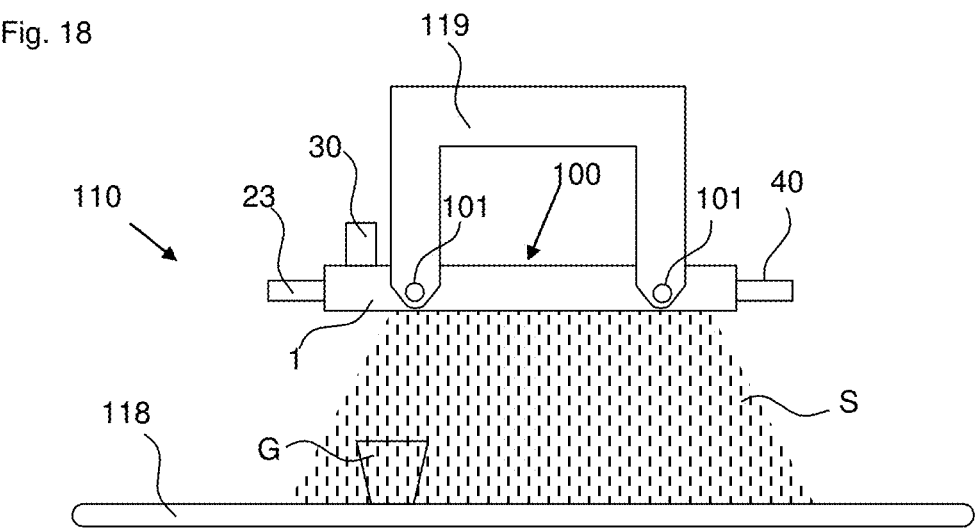
FIG. 18 shows a schematic side view onto a device according to a further embodiment having a surface radiator for disinfection.

A surface radiator 100 can be used for lighting, for carrying out a photochemical reaction or for disinfection—depending on the emission spectrum of the used LEDs 2—which is why the arrangement of the inlet opening 3 and of the return opening 4 as well as of the connecting opening 16b on the hosing body 1 be a function of an installation context of the surface radiator 100 in a corresponding lighting, photochemical reactor or disinfection device. As in the example of FIGS. 1 to 10 and 12 to 14, the inlet opening 3 and the return opening 4 can thus be arranged jointly on a side surface of the housing body 1. As shown in the example of FIGS. 1 to 8 and 10, the connecting opening 16b can also be arranged on the same side surface as the inlet opening 3 and the return opening 4. The exemplary embodiment of the surface radiator 100 in FIG. 11 shows an arrangement of the inlet opening 3 and of the return opening 4 on the rear side of the housing body 1, as well as in the case of the surface radiator 100 of the device 110 in FIG. 17, as can be seen there from the illustrated inlet and return connecting element 30, 40, which are each connected to an inlet and return opening not illustrated there. FIG. 17 further shows a connecting plug 23, which is arranged in the connecting opening not illustrated there on the rear side of the housing body 1. However, inlet, return and connecting opening 3, 4, 16b can also be arranged on different sides of the housing body 1, as can be seen in an exemplary manner on the surface radiator 100 of the device 110, which is illustrated in FIG. 18, where an inlet connecting element 30, which is connected to an inlet opening not illustrated there, is arranged on the rear side of the housing body 1, while the return connecting element 40, which is connected to a return opening not illustrated there, and the connecting plug 23, which is arranged in the connecting opening not illustrated there, are arranged on side surfaces of the housing body 1 facing away from one another. However, a device 110 is not limited to the arrangement of inlet, return and connecting opening 3, 4, 16b, which are illustrated in the examples—said device can be based on the respective installation context and can vary accordingly.

Due to the fact that the active cooling by means of the direct contact of the LEDs with the coolant allows for the use of surface radiators with a plurality of LEDs or the operation thereof with highest performance, respectively, a high performance density is attained, which can compete with low pressure and medium pressure radiators in the field of photochemistry. The handling and managing the heat balance—thermal management in short—of an LED surface radiator, which has to also take into account the process temperature of a reaction medium, which adjoins the emission window of the surface radiator, is of vital importance for an adequate service life of the LED.

FIG. 17 clarifies a first example of a device 110, which is formed for carrying out a photochemical reaction by means of a surface radiator 100, the LEDs 2 of which provide an emission spectrum for carrying out the photochemical reaction. The device 110 for carrying out a photochemical reaction is a photoreactor, the housing of which comprises a reactor vessel 111 and a reactor cover 112. In the illustrated example, the installation space provided for the surface radiator 100 is provided in the reactor cover 112—other reactor devices can also provide installation spaces in a wall of the reactor vessel 111. A reactor device 110 can further have several installation spaces for several surface radiators. For the installation into the reactor cover 112, the housing body 1 of the surface radiator 100 has fastening bores 101 (see also FIGS. 1 and 10) as installation elements, so that the surface radiator 100 can be fastened in the reactor cover 112 by means of screws or bolts. In order to also attain an optimal cooling of the LEDs 2 here, in that heat is dissipated outside of the surface radiator 100, the coolant, which does not only absorb the heat generated by the LEDs 2 but also the heat from exothermic reactions from the reaction chamber adjoining the emission window 5, is circulated, which leads from the return connecting element 40 via a coolant return line 114 in the circulation line 116, which comprises a pump and optionally heat exchangers and/or fittings, such as valves, etc., for instance for the adaptation of the pressure in the emission chamber, and via a coolant supply line 113 to the inlet connecting element 30. The electrical connection of the surface radiator 100 by means of the connecting plug 23 via a connecting cable 115 to a power supply and control device 117 is further illustrated. The power supply and control device 117, which can comprise, for example, ballast or power electronics, drivers—unless accommodated on the printed circuit board or in the connecting chamber—and power supply units, can be an external power supply and control device.

In the case of the device 110 illustrated in FIG. 18, the surface radiator 100 comprising the inlet and return connecting elements 30, 40 as well as the connecting plug 23 is illustrated, wherein the device 110 can also have a circulation, which is not illustrated here, for the coolant from the return connecting element 40 via a return, circulating, supply line to the inlet connecting element 30 according to FIG. 17. The device 110 can further have an illustrated power supply for the surface radiator 100, which can be connected to the connecting plug 23, e.g., via a connecting cable. The exemplary device 110 illustrated in FIG. 18 is formed for disinfection of the surface of objects G, wherein the front side of the surface radiator 100 points in the direction of a conveyor belt 118, on which the objects G, which are to be disinfected, are conveyed through underneath the surface radiator 100, so that the incident radiation S emitted in the emission region of the surface radiator 100, which, for disinfection, lies within the UV-C spectral range, hits the surface of the object G during the conveying and eliminates germs, which are present there. The installation context of the surface radiator 100 in this device 110 for disinfection comprises a holder 119 as housing, by means of which the surface radiator 100 is arranged at a predetermined distance above the conveyor belt 118, the surface radiator 100 has, for this purpose, fastening bores 101 on the housing body 1 (see also FIGS. 1 and 10), which can engage, for example, with pins or screws for fastening to the holder 119.

Type and number of the installation elements are to not be limited to the illustrated fastening bores because the type and number of the installation elements can also be a function of the installation context as well as the size and design of the surface radiator 100. All installation elements can be embodied for forming a—preferably releasable—plug, screw, plug/screw, clamping connection or the like. Alternative or additional non-illustrated installation elements can be, for example, and not exclusively, pins, tabs, collars, webs or flanges or also shaped protrusions or shaped recesses for engagement with corresponding counter shaped elements, which can support or simplify the installation of the surface radiator 100 into a device 110.

The scope of protection of the present invention is to not be limited to the two illustrated examples of a device, which comprise a surface radiator 100.

A surface radiator with improved cooling can serve for any use for lighting, for carrying out a photochemical reaction or for disinfection with LED, the emission spectrum of having a corresponding incident radiation for lighting, for carrying out a photochemical reaction or for disinfection. Devices for lighting as well as a device deviating from the illustrated examples for carrying out a photochemical reaction or for disinfection, which comprise a surface radiator, are accordingly also captured by the scope of protection.

With regard to the operation of a surface radiator 100 with circulation of the coolant in a photoreactor or a device for carrying out a photochemical reaction, respectively, it is important to ensure that the flow rate, in particular in the case of silicone oil, is kept low, i.e., preferably below 1 m/s because an electrostatic charge with the risk of the formation of an ignition source can otherwise occur in the case of a product, which is non-conductive and which is present in the photoreactor. In order to meet the current demands for an ATEX certification with respect to the ignition protection type "o"=oil encapsulation, the coolant has to have a kinematic viscosity (at 25° C.) of at least 20 cSt, even if coolant with lower viscosity of, for example, 5 cSt, would be technically more advantageous with regard to the circulation and adherence to the surface temperatures of the LED. The coolant can thus have a kinematic viscosity (at 25° C.) of 5 to 60 cSt, wherein, with regard to the current standards with respect to the explosion protection, a viscosity in the range of 20 to 50 cSt is preferred in order to obtain a corresponding certification. When using coolants with high viscosity, it is further advantageous to dimension the return and inlet connecting lines with sufficiently large diameter to avoid internal pressure losses, in order to avoid a pressure on the LEDs, which is too high.

In a further embodiment, for controlling the flow speed of the coolant due to the fact that the flow volume of the circulated coolant should not fall below a predetermined minimum value, the surface radiator or the higher-ranking device, respectively, can, in order to maintain the surface temperature of the LEDs, additionally have a flowmeter, which is connected to a control unit, which is configured to control a pump and/or fitting (valve), which is connected to the return and inlet connecting lines, as a function of the flow value measured by means of the flowmeter, in order to maintain a predetermined flow speed of the coolant through the emission chamber along a surface of the LED. The control unit can be a separate unit, part of the flowmeter, part of the pump or of the fitting or part of a control device of the higher-ranking device. Due to the high viscosity required for the explosion protection and the flow speed, which is to be kept low, mass flowmeters, for example a Coriolis mass flowmeter or variable area flowmeters or other suitable measuring methods, can preferably be used, whereas vortex measuring devices are rather unsuitable. For the high viscosities and low flow speeds required for the ATEX certification, in particular Coriolis mass flowmeters are suitable as flowmeters, which meet the safety integrity level (SIL in short) for an ATEX certification. However, the variable area flowmeters, which can be used alternatively, also provide reliable measuring values in the case of high viscosity and low flow speed of the coolant. In one of the circulation or coolant connecting lines, respectively, a breathing unit with drying means can be provided, preferably at a highest point, in order to provide for a ventilation of the coolant for avoiding condensation, wherein an input of moisture by means of fresh air can be avoided by means of a drying agent, such as, for example, silica gel.

In order to decouple the LEDs from the conditions prevailing in the surrounding area adjoining the emission window, and so as not to impact the functionality of the LEDs, the emission window can be a double-walled emission window, or the surface radiator or the higher-ranking device, respectively, can have a second emission window, which covers the emission window delimiting the emission chamber. The gap formed between the two emission windows or the double walls provides a further thermal decoupling. The latter can even be intensified in that a negative pressure is generated in the gap by means of a suction device or in that a further cooling circuit for the fluid cooling is connected in the gap. In the case of the embodiment as double-walled emission window, the gap between the walls can also already be evacuated in response to the production thereof. All of the liquid or gaseous fluids, which are transparent for the incident radiation, for example water, inert gas, such as nitrogen or also air, are suitable as cooling fluid.

In some embodiments, a surface radiator can have several printed circuit boards, each with a partial number of the totality of the LED—also as a function of the number of the used LEDs—wherein the printed circuit boards can be controlled individually. This makes it possible that in the event of a failure of an LED on a printed circuit board, not all LEDs have to be turned off but only the affected printed circuit board, while the other printed circuit boards can still remain in operation. A replacement of the affected printed circuit board can be postponed to a suitable point in time, for instance after a photochemical reaction carried out by means of the surface radiator has ended. For this purpose, the surface radiator can have a detection unit for each printed circuit board, which is configured to determine a failure of one or several LED(s) on a printed circuit board and to interrupt the power supply for the affected printed circuit board as a function of a determined failure and to optionally delimit it accordingly for the further printed circuit boards. A warning message can optionally also be output via the control device of the surface radiator or the higher-ranking device, respectively, when the detection unit is connected to the power supply and control device. Such a detection unit is generally also conceivable for each LED, so that the respective power supply is interrupted and the power supply for the further LEDs is optionally delimited correspondingly in the event of the failure of individual LEDs, so that it is avoided that an LED failure, which is accompanied by a temperature hotspot, leads to a chain reaction with the failure of further LEDs as a result of an excessive boundary temperature.

The surface radiator can further have one or several temperature sensor(s), which is/are arranged on the housing body or a printed circuit board and is/are connected to the power supply and control device, which comprises a circuit breaker for the LEDs. The circuit breaker ensures a protective shut-down for the protection of the semiconductor components, when the maximally permissible ambient temperature is exceeded. If the LEDs or LED groups, respectively, of a surface radiator can be controlled individually and if a temperature sensor is in each case assigned to an LED or LED group, respectively, the control device can turn off the LEDs or the LED group, respectively, assigned to this sensor when one of the sensors determines an exceeding of the maximum temperature. The control device can accordingly switch on the corresponding LED/LED group again automatically when it is determined by the sensor that the maximum temperature is fallen below as a result of the protective shut-down. All safety-relevant sensors of the surface radiator, such as the detection units and temperature sensors, can be embodied redundantly or in two channels, respectively, in order to realize the correspondingly necessary SIL class.

The power supply and control device can further alternatively or additionally have at least one control circuit for the LED control, by means of which similar or different LEDs can be dimmed and/or the spectrum of the emitted wavelengths of different LEDs can be changed, in order to adapt the emitted light quantity or the emitted wavelengths on request or as necessary. Use- or process-specific spectra, respectively, can thus be provided, wherein the radiation intensity can further be adapted to the use, e.g., photochemical process, by means of control circuit. In a device for carrying out a photochemical reaction, e.g., a performance control of the LED (dimming) can thus take place for the process control because the absorption changes during the process in many reactions. This can be responded to by means of systematic measuring and control circuits and LED dimming, in order to realize an efficient system and to avoid over-radiation.

A surface radiator can have monochromatic LEDs as well as a mixture of LEDs with different emission spectra, which provide an optimal incident radiation, which corresponds to an optimal utilization of the absorption spectrum of the respective reaction when carrying out a photochemical reaction or disinfection. The same applies when the device for carrying out a photochemical reaction is a bioreactor. LEDs with different emission wavelengths can be implemented here, in order to attain optimal growth rates. In different growth phases or for different cells, respectively, optimally mixed light spectra and intensities can in each case be used for the optimized growth.

LIST OF REFERENCE NUMERALS 1 housing body
2 light-emitting semiconductor component (LED)
2a, 2b, 2c, primary optics, semiconductor crystal, wire,
2d, 2e, 2f, 2g anode, LED chip, cathode, base structure
3 inlet opening
4 return opening
5 emission window
6 emission chamber
10, 10a, 10b first cooling channel, distributor channel section close to the inlet, distributor channel spaced apart from the inlet
11, 11a second cooling channel, collecting channel section
12 fastening surface
12a, 12b fastening ledge
13 orifice opening
14 discharge opening
15 connecting chamber
16a, 16b passage opening, connecting opening
17, 17a holding frame, opening
18, 18a seal, sealing groove
19 fastening bore
20 printed circuit board
21 connecting contact pair
22 connecting line
23 connecting plug
24 driver/ballast
30 inlet connecting element
40 return connecting element
50 fastening means
60 adhesive layer
100 surface radiator
101 installation element
110 device for lighting, for carrying out a photochemical reaction or for disinfection
111 reactor vessel
112 reactor cover
113 coolant supply line
114 coolant return line
115 connecting cable
116 circulation line (comprising pump and optionally heat exchanger)
117 power supply and control device
118 conveyor belt
119 holder
a fluid path
G treatment object
K electrically insulating coolant
S incident radiation

The invention claimed is:

1. A surface radiator (100), comprising:
 a plurality of light-emitting semiconductor components (2); and
 a housing body (1),
 wherein the housing body (1) has a cooling channel (10, 11) for a coolant, the cooling channel (10, 11) including a first cooling channel (10) and a second cooling channel (11),
 wherein the cooling channel (10, 11) forms at least a part of a fluid path (a),
 wherein the fluid path (a) extends from an inlet opening (3) to a return opening (4),
 wherein the inlet opening (3) and the return opening (4) are formed on the housing body (1),
 wherein an emission window (5) overlies the light-emitting semiconductor components (2),
 wherein the emission window (5) defines a front side of the surface radiator (100),
 wherein the emission window (5) is transparent for an incident radiation(S),
 wherein the incident radiation(S) can be emitted by the light-emitting semiconductor components (2),
 wherein the emission window (5) is arranged on the housing body (1),
 wherein the housing body (1) provides a fastening surface (12) for the light-emitting semiconductor components (2),
 wherein the fastening surface (12) is spaced apart from the emission window (5),
 wherein the emission window (5) is arranged on the housing body (1) in a fluid-tight manner,
 wherein the housing body (1), the light-emitting semiconductor components (2), and the emission window (5) delimit an emission chamber (6),
 wherein the fluid path (a) is defined by
  i) the first cooling channel (10) extending from the inlet opening (3) through the housing body (1) to an orifice opening (13) formed on a first side adjacent to the fastening surface (12), and
  ii) the emission chamber (6) from the orifice opening (13) to a discharge opening (14) formed on a second side facing away from the first side adjacent to the fastening surface (12), and
  iii) the second cooling channel (11) extending from the discharge opening (14) through the housing body (1) to the return opening (4),
 wherein the coolant (K) is an electrically insulating liquid,
 wherein the electrically insulating liquid is transparent for the incident radiation(S), wherein a connecting chamber (15) is formed on the front side in the housing body (1) adjacent to the fastening surface (12),
wherein the connecting chamber (15) is open to the emission chamber (5),
wherein a connecting opening (16b) is formed on the housing body (1),
wherein the connecting opening (16b) is connected to the connecting chamber (15),
wherein a connecting line (22) for connecting the light-emitting semiconductor components (2) extends into the connecting chamber (15),
wherein a ballast is provided on a printed circuit board (20),
wherein the plurality of light-emitting semiconductor components (2) is fastened to the fastening surface (12) by the printed circuit board (20),
wherein a pair of connecting contacts (21) for a row of the light-emitting semiconductor components (2) is in each case formed on a side of the printed circuit board (20) close to the connecting chamber (15),
wherein each connecting contact (21) is connected to a respective connecting line (22) and the ballast is provided between the connecting contacts (21) and the light-emitting semiconductor components (2) or
the ballast (24) for the light-emitting semiconductor components (2) is arranged in the connecting chamber (15), connected to the connecting line (22).

2. The surface radiator (100) according to claim 1,
wherein the housing body (1) is formed for the arrangement of the surface radiator (100) in a device (110) for lighting, for carrying out a photochemical reaction, or for disinfection,
wherein the housing body (1) has a rear side facing away from the front side and is delimited between front side and rear side by side surfaces, and
wherein the inlet opening (3) and the return opening (4) are arranged jointly on one of the side surfaces or the rear side or individually on different side surfaces or on one of the side surfaces and the rear side.

3. The surface radiator (100) according to claim 1,
wherein the orifice opening (13) is formed on a side of the fastening surface (12) facing away from the inlet opening (3),
wherein the first cooling channel (10) runs through the housing body (1) at least partly in a plane parallel to the fastening surface (12),
wherein the discharge opening (14) is formed on a side of the fastening surface (12) close to the return opening (4).

4. The surface radiator (100) according to claim 1,
wherein the inlet opening (3) is fluidically connected to a distributor channel section (10a) close to the inlet opening (3),
wherein several first cooling channels (10) extend from the distributor channel section (10a) to corresponding orifice openings (13) on a side of the fastening surface (12) spaced apart from the inlet opening (3), and
wherein the second cooling channel (11) extends from a collecting channel section (11a), which is connected to a plurality of discharge openings (14), to the return opening (4).

5. The surface radiator (100) according to claim 1,
wherein the first cooling channel (10) extends from the inlet opening (3) to a distributor channel section (10b) spaced apart from the inlet opening (3),
wherein a plurality of orifice openings (13) is formed on the distributor channel section (10b),
wherein the second cooling channel (11) extends from a collecting channel section (11a) to the return opening (4), and
wherein the collecting channel section (11a) is connected to a plurality of discharge openings (14).

6. The surface radiator (100) according to claim 1,
wherein the surface radiator (100) has a holding frame (17),
wherein the holding frame (17) is arranged on the housing body (1) for holding the emission window (5),
wherein the holding frame (17) is formed for leaving the light-emitting semiconductor components (2) uncovered, and
wherein a circumferential seal (18) is arranged between the holding frame (17) and the emission window (5) and between the emission window (5) and the housing body (10).

7. The surface radiator (100) according to claim 1,
wherein the emission window (5) is fastened to the housing body (1) by an adhesive layer (60).

8. The surface radiator (100) according to claim 1,
wherein the housing body (1) has a fastening ledge (12a, 12b) on the front side,
wherein the fastening ledge (12a, 12b) surrounds the fastening surface (12),
wherein the fastening ledge (12a) is formed for receiving the emission window (5) and
wherein a distance of the fastening ledge (12a) from the fastening surface (12) defines a height of the emission chamber (6).

9. The surface radiator (100) according to claim 1,
wherein the connecting opening (16b) is connected to the connecting chamber (15) via a passage opening (16a), and
wherein a cross sectional surface of the passage opening (16a) is smaller than a cross sectional surface of the connecting opening (16b).

10. The surface radiator (100) according to claim 1,
wherein the connecting line (22) extends at least partly into the connecting opening (16b),
wherein the connecting line (22) is sealed in the connecting opening (16b) by a casting or solder compound.

11. The surface radiator (100) according to claim 1,
wherein a connecting plug (23) is connected to the connecting line (22),
wherein the connecting plug (23) extends at least partly into the connecting opening (16b), and
wherein the connecting plug (23) is sealed in the connecting opening (16b) by a casting or solder compound.

12. The surface radiator (100) according to claim 1,
wherein the surface radiator (100) has an inlet connecting element (30) and a return connecting element (40),
wherein the inlet connecting element (30) is connected to the inlet opening (3),
wherein the return connecting element (40) is connected to the return opening (4), and
wherein the connection of the inlet connecting element (30) to the inlet opening (3) and/or of the return connecting element (40) to the return opening (4) is sealed by a casting or solder compound.

13. A device (110) for lighting, for carrying out a photochemical reaction, or for disinfection, comprising
the surface radiator according to claim 1,
wherein an emission spectrum of the light-emitting semiconductor components (2) provides the incident radiation(S) for lighting, for heating, for carrying out a photochemical reaction, or for disinfection.

14. The device (110) according to claim 13,
wherein the device (110) has a housing (111, 112, 119),
wherein the housing (111, 112, 119) at least partly surrounds a lighting chamber, reaction chamber or disinfection chamber and has at least one installation space for the surface radiator (100), and
wherein the housing body (1) of the surface radiator (100) has an installation element (101) for arrangement in the device (110).

\* \* \* \* \*